/

US008759492B2

(12) United States Patent
Lin et al.

(10) Patent No.: US 8,759,492 B2
(45) Date of Patent: Jun. 24, 2014

(54) ENGINEERED RED-SHIFTED CHANNELRHODOPSIN VARIANTS

(75) Inventors: John Yu-luen Lin, Del Mar, CA (US); Roger Y. Tsien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 118 days.

(21) Appl. No.: 13/588,957

(22) Filed: Aug. 17, 2012

(65) Prior Publication Data

US 2013/0066402 A1    Mar. 14, 2013

Related U.S. Application Data

(60) Provisional application No. 61/524,618, filed on Aug. 17, 2011.

(51) Int. Cl.
*A61K 36/00* (2006.01)
*C12P 21/08* (2006.01)

(52) U.S. Cl.
USPC ...................................... 530/387.3; 530/370

(58) Field of Classification Search
None
See application file for complete search history.

(56) References Cited

U.S. PATENT DOCUMENTS

| 5,776,689 A | 7/1998 | Karin et al. | |
|---|---|---|---|
| 2013/0224821 A1* | 8/2013 | Deisseroth et al. | 435/173.4 |

OTHER PUBLICATIONS

Adamantidis, A.R. et al., "Neural substrates of awakening probed with optogenetic control of hypocretin neurons," *Nature*, Nov. 15, 2007, vol. 450, pp. 420-425.
Aravanis, A.M. et al., "An optical neural interface: in vivo control of rodent motor cortex with integrated fiberoptic and optogenetic technology," *Journal of Neural Engineering*, 2007, vol. 4, pp. S143-S156.
Arrenberg, A.B. et al., "Optogenetic Control of Cardiac Function," *Science*, Nov. 12, 2010, vol. 330, pp. 971-974.
Bell, J.R. et al., "Photoactivites of the Red-Shifted Azulenic Bacteriorhodopsin Analogues," *J. Phys. Chem. A*, 1998, vol. 102, pp. 5481-5483.
Berg, R.W. et al., "Vibrissa Movement Elicited by Rhythmic Electrical Microstimulation to Motor Cortex in the Aroused Rat Mimics Exploratory Whisking," *J Neurophysiol*, 2003, vol. 90, pp. 2950-2963.
Berndt, A. et al., "Bi-stable neural state switches," *Nature Neuroscience*, Feb. 2009, vol. 12, No. 2, pp. 229-234.
Berndt, A. et al., "High-efficiency channelrhodopsins for fast neuronal stimulation at low light levels," *PNAS*, May 3, 2011, vol. 108, No, 18, pp. 7595-7600.
Boyden, E.S. et al., "Millisecond-timescale, genetically targeted optical control of neural activity," *Nature Neuroscience*, Sep. 2005, vol. 8, No. 9, pp. 1263-1268.
Brecht, M. et al., "Whisker movements evoked by stimulation of single pyramidal cells in rat motor cortex," *Nature*, Feb. 19, 2004, vol. 427, pp. 704-710.

Bruegmann, T. et al., "Optogenetic control of heart muscle in vitro and in viva," *Nature Methods*, Nov. 2010, vol. 7, No. 11, pp. 897-900, Online Methods, 3 pages.
Buss, J.E. et al., "The Six Amino-Terminal Amino Acids of p60$^{src}$ are Sufficient to Cause Myristylation of p32v$^{-ras}$," *Molecular and Cellular Biology*, Sep. 1988, vol. 8, No. 9, pp. 3960-3963.
Drew, P.J. et al., "Chronic imaging and manipulation of cells and vessels through a polished and reinforced thinned-skull," *Nat Methods*, Dec. 2010, vol. 7, No. 12, pp. 981-984.
Drew, P.J. et al., "Chronic optical access through a polished and reinforced thinned skull," *Nature Methods*, Dec. 2010, vol. 7, No. 12, pp. 981-984.
Govorunova, E.G. et al., "New Channelrhodopson with a Red-Shifted Spectrum and Rapid Kinetics from *Mesostigma viride*," *mBio*, May/Jun. 2011, vol. 2, No. 3, pp. 1-9.
Gradinaru, V. et al., "Molecular and Cellular Approaches for Diversifying and Extending Optogenetics," *Cell*, Apr. 2, 2010, vol. 141, pp. 154-165.
Grandinaru, V. et al., "Targeting and Readout Strategies for Fast Optical Neural Control In Vitro, and In Vivo," *The Journal of Neuroscience*, Dec. 26, 2007, vol. 27, No. 52, pp. 14231-14238.
Grutzendler, J. et al., "Long-term dendritic spine stability in the adult cortex," *Nature*, Dec. 2002, vol. 420, pp. 812-816.
Gunaydin, L.A. et al., "Ultrafast optogenetic control," *Nature Neuroscience*, Mar. 2010, vol. 13, No. 3, pp. 387-392, Online Methods, 1 page.
Haiss, F, et al., "Spatial Segregation of Different Modes of Movement Control in the Whisker Representation of Rat Primary Motor Cortex," *The Journal of Neuroscience*, Feb. 9, 2005, vol. 25, No. 6, pp. 1579-1587.
Hancock, J.F. et al., "A CAAX or a CAAL motif and a second signal are sufficient for plasma membrane targeting if ras protein," *The EMBO Journal*, 1991, vol. 10, No. 13, pp. 4033-4039.
Hauss-Wegrzyniak, B. et al., "Chronic Brain Inflammation Results in Cell Loss in the Entorhinal Cortex and Impaired LTP in Perforant Path-Granule Cell Synapses," *Experimental Neurology*, 2002, vol. 176, pp. 336-341.
Hubbard, R. et al., Chapter 243: Methodology of Vitamin A and Visual Pigments,: in *Methods in Enzymology*, vol. XVIII, Vitamins and Coenzymes, Part C, Donald B. McCormick et al., eds., 1971, Academic Press, Inc.: New York, NY, pp. 615-653.
Kato, H.E. et al., "Crystal structure of the channelrhodopsin light-gated cation channel," *Nature*, Feb. 16, 2012, vol. 482, pp. 369-374, Methods, 1 page.
Kleinlogel, S. et al., "Ultra light-sensitive and fast neuronal activation with the $Ca^{2+}$—permeable channelrhodopsin CatCh," *Nature Neuroscience*, Apr. 2011, vol. 14, No. 4, pp. 513-518, Online Methods, 2 pages.
Knöpfel, T. et al., "Toward the Second Generation of Optogenetic Tools," *The Journal of Neuroscience*, Nov. 10, 2010, vol. 30, No. 45, pp. 14998-15004.

(Continued)

*Primary Examiner* — Suzanne M Noakes
*Assistant Examiner* — Jae W Lee
(74) *Attorney, Agent, or Firm* — Morgan, Lewis & Bockius LLP

(57) ABSTRACT

The invention provides engineered red-shifted channelrhodopsin variants. In some embodiments, the channelrhodopsin variants are characterized by improved membrane trafficking, expression, and/or unique spectral and kinetic properties.

12 Claims, 22 Drawing Sheets
(17 of 22 Drawing Sheet(s) Filed in Color)

(56) References Cited

OTHER PUBLICATIONS

Liebman, P. et al., "Cyanopsin, a Visual Pigment of Retinal Origin," *Nature*, Nov. 4, 1967, vol. 216, pp. 501-503.

Lin, J.Y. et al,, "Characterization of Engineered Channelrhodopsin Variants with Improved Properties and Kinetics," *Biophysical Journal*, Mar. 2009, vol. 96, pp. 1803-1814.

Lin, J.Y. et at, "Development and characterization of channelrhodopsin variants for improved optical control of neuronal excitability," *Neuroscience 2009*, Oct. 19, 2009, Presentation Abstract, 2 pages.

Lin, J.Y., "A user's guide to channelrhodopsin variants: features, limitations and future developments," *Experimental Physiology*, 2011, vol. 96.1, pp. 19-25.

Matz, M.V. et al., "Fluorescent proteins from nonbioluminescent *Anthozoa* species," *Nature Biotechnology*, Oct. 1999, vol. 17, pp. 969-973.

Nagel, G. et al., "Channelrhodopsin-1: A Light-Gated Proton Channel in Green Algae," *Science*, Jun. 28, 2002, vol. 296, pp. 2395-2398.

Nagel, G. et al., "Channelrhodopson-2, a directly light-gated cationh-selective membrane channel," *PNAS*, Nov. 25, 2003, vol. 100, No. 24, pp. 13940-13945.

Nagel, G. et al., "Light Activation of Channelrhodopsin-2 in Excitable Cells of *Caenorhabditis elegans* Triggers Rapid Behavioral Responses," *Current Biology*, Dec. 20, 2005, vol. 15, pp. 2279-2284.

Osakada, F. et al., "New Rabies Virus Variants for Monitoring and Manipulating Activity and Gene Expression in Defined Neural Circuits," *Neuron*, Aug. 25, 2011, vol. 71, pp. 617-631.

Shaner, N.C. et al., "A guide to choosing fluorescent proteins," *Nature Methods*, Dec. 2005, vol. 2, No. 12, pp. 905-909.

Sohler, T.P. et al., "The Pial Circulation of Normal, Non-Anesthetized Animals, Part 1. Description of a Method of Observation," *Journal of Pharmacology and Experimental Therapeutics*, 1941, vol. 71, pp. 325-330.

Tromberg, B.J. et al., "Non-invasive In Vivo Characterization of Breast Tumors Using Photon Migration Spectroscopy," *Neoplasia*, Jan.-Apr. 2000, Nos. 1-2, p. 26-40.

Wang, H. et al., "Molecular Determinants Differentiating Photocurrent Properties of Two Channelrhodopsins from *Chlamydomons*," *The Journal of Biological Chemistry*, Feb. 27, 2009, vol. 284, No. 9, pp. 5685-5696.

Wen, L. et al., "Opto-Current-Clamp Actuation of Cortical Neurons Using a Strategically Designed Channeirhodopsin," *PLoS One*, Sep. 2010, vol. 5, No. 9, pp. 1-13.

Xu, H-T. et al., "Choice of cranial window type for in vivo imaging affects dendritic spine turnover in the cortex," *Nature Neuroscience*, May 2007, vol. 10, No. 5, pp. 549-551.

Yizhar, O. et al., "Neocortical excitation/inhibition balance in information processing and social dysfunction," *Nature*, Sep. 8, 2011, vol. 477, pp. 171-178.

Zhang, F. et al., "Red-shifted optogenetic excitation: a tool for fast neural control derived from *Volvox carteri*," *Nat Neurosci*, Jun. 2008, vol. 11, No. 6, pp. 631-633.

\* cited by examiner

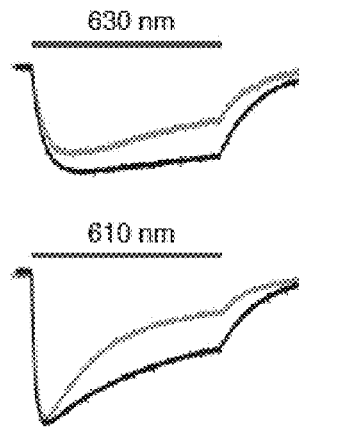
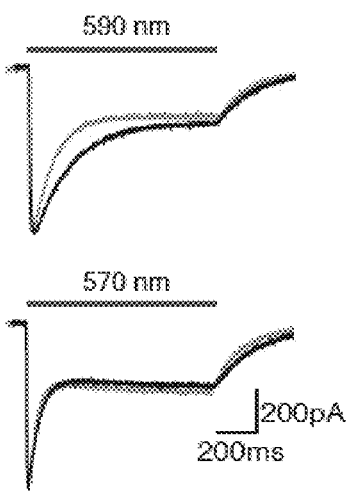
FIG. 2A
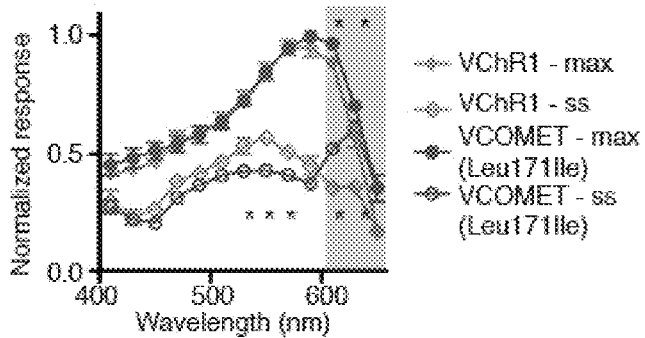
FIG. 2B
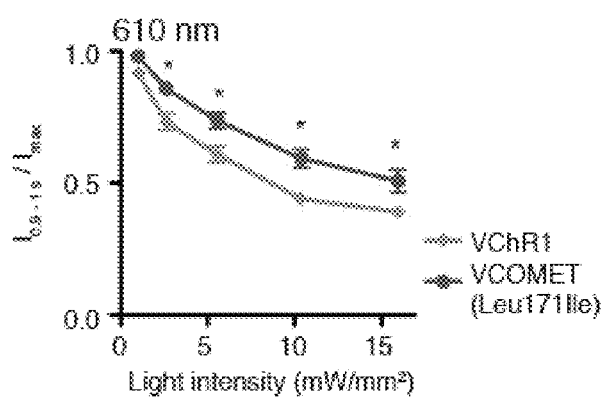
FIG. 2C
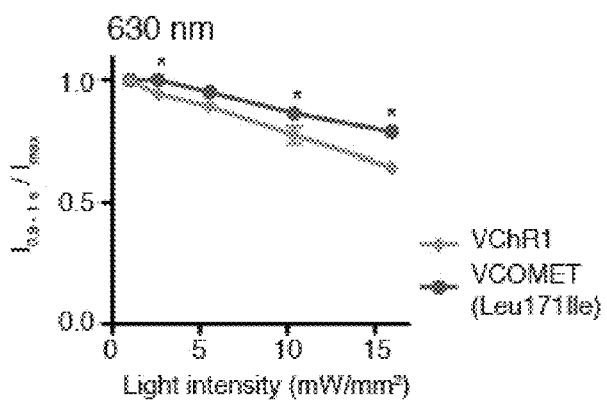
FIG. 2D

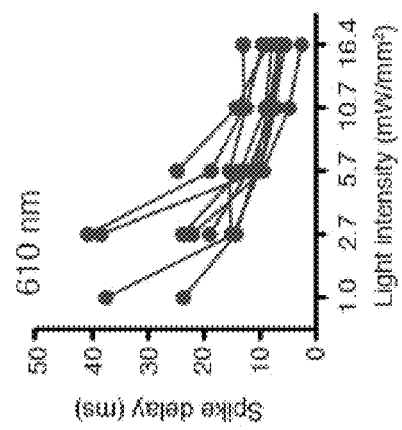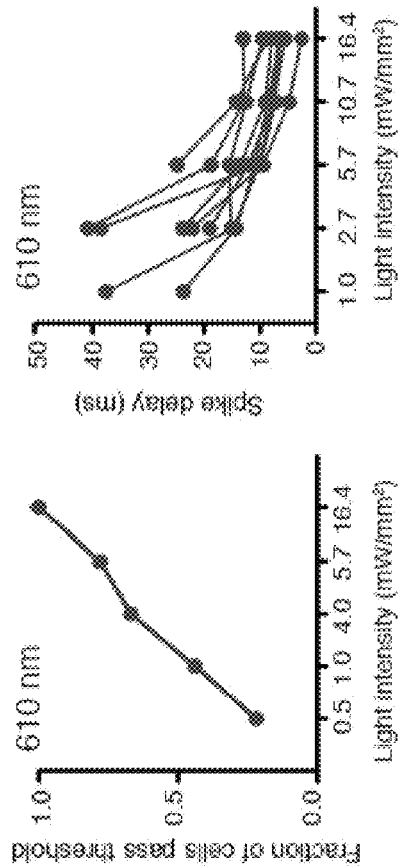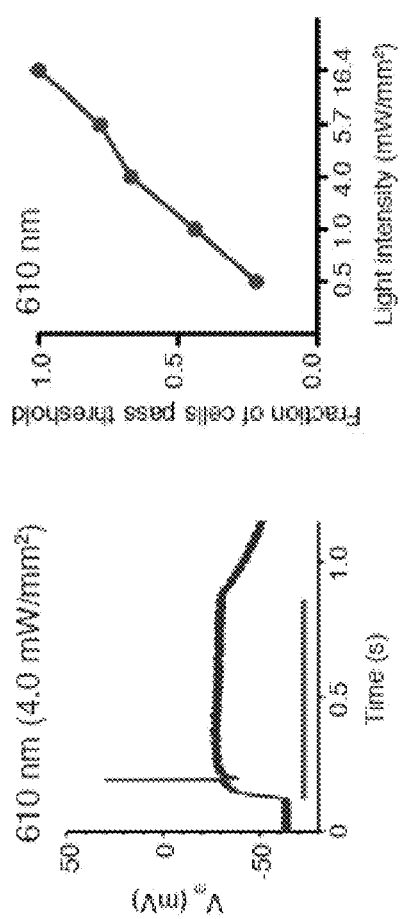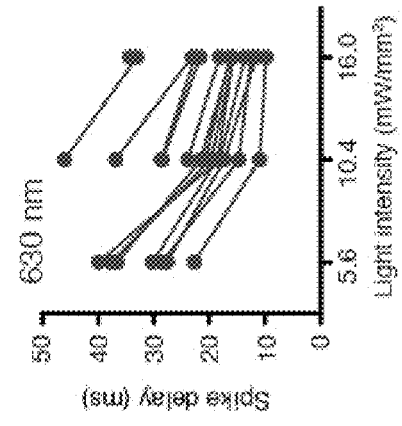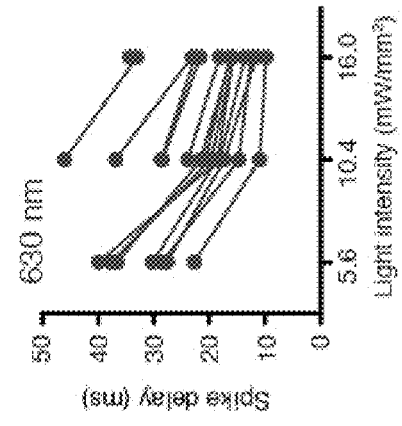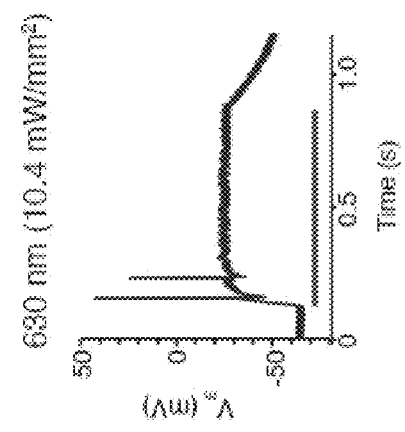
FIG. 3A  FIG. 3B  FIG. 3C
FIG. 3D  FIG. 3E  FIG. 3F

FIG. 5

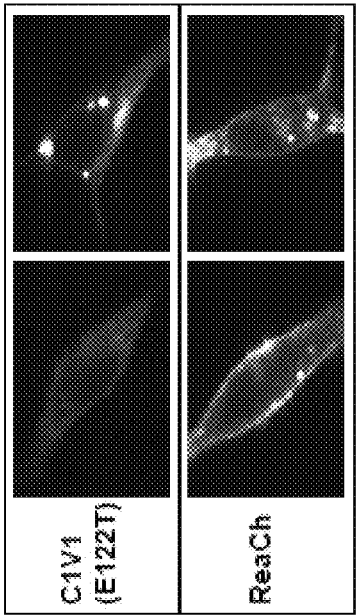
FIG. 6A
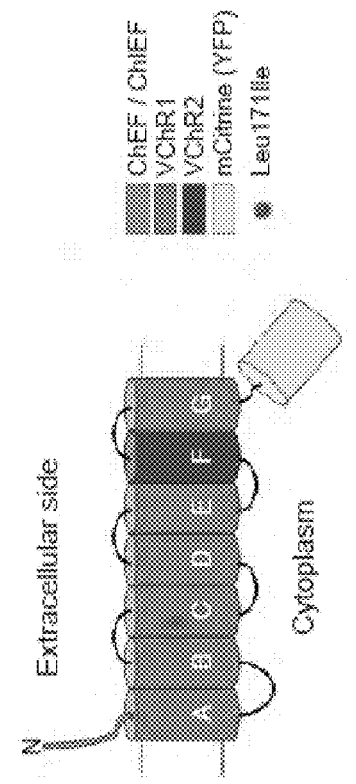
FIG. 6B
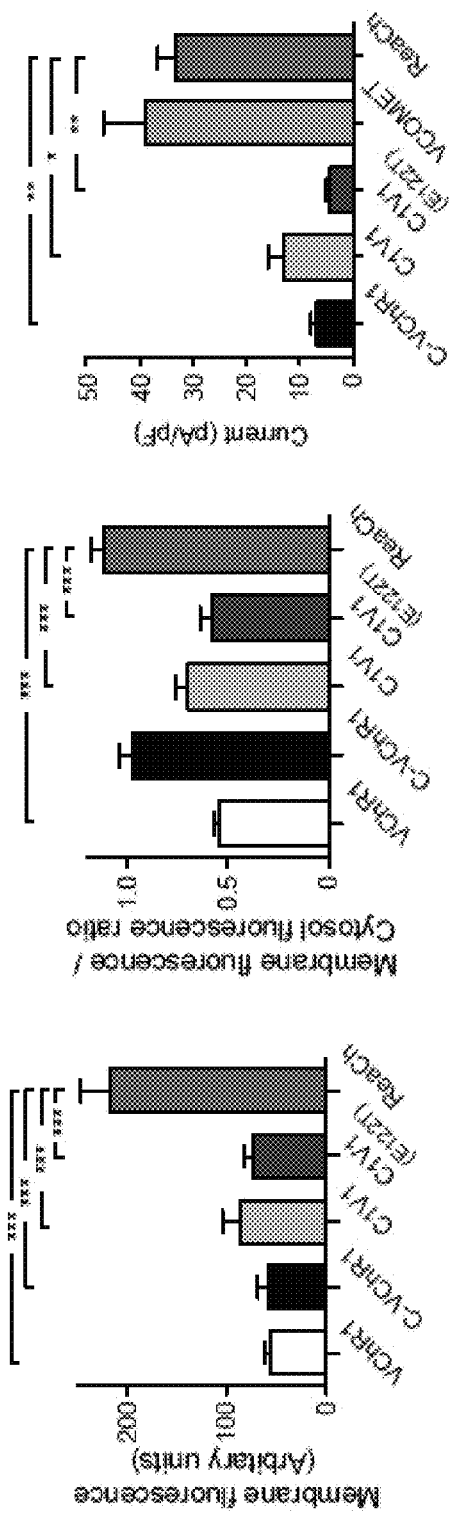
FIG. 6C
FIG. 6D
FIG. 6E

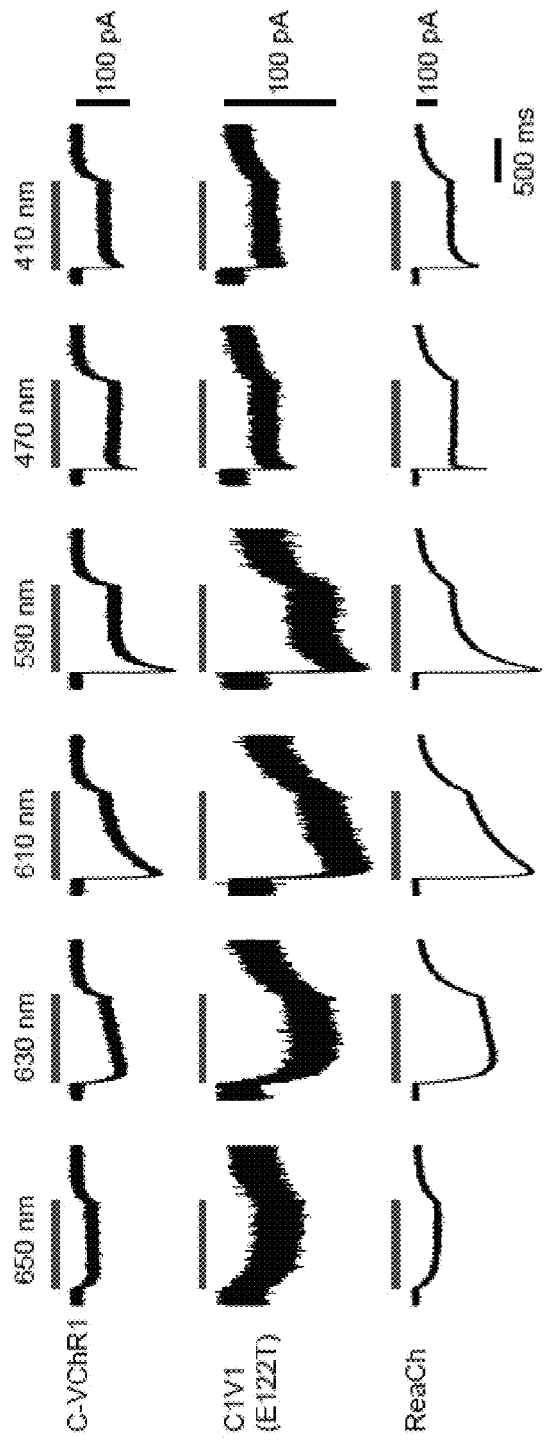
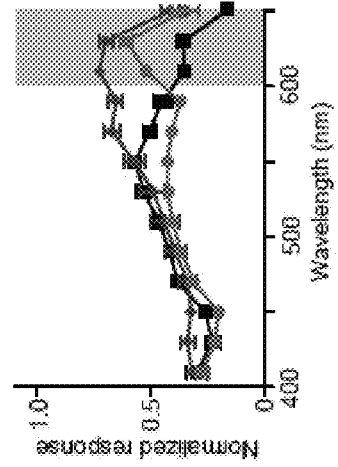
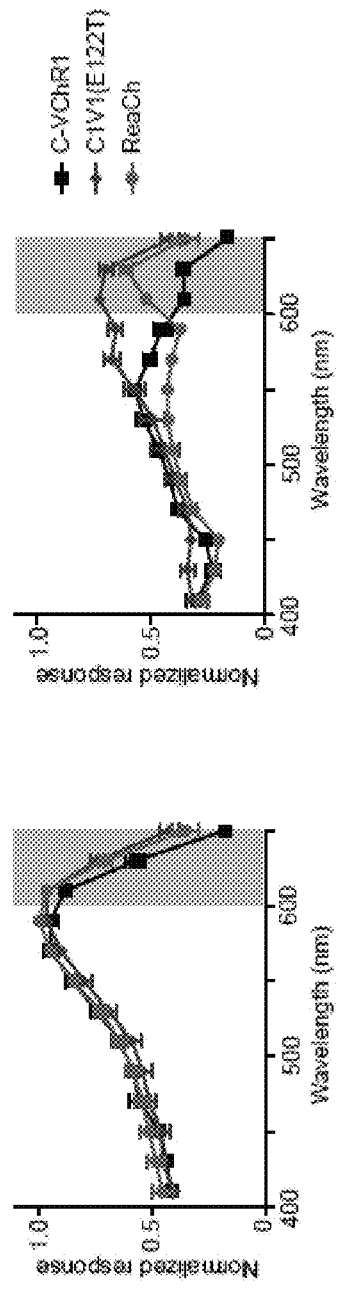
FIG. 6F
FIG. 6G
FIG. 6H

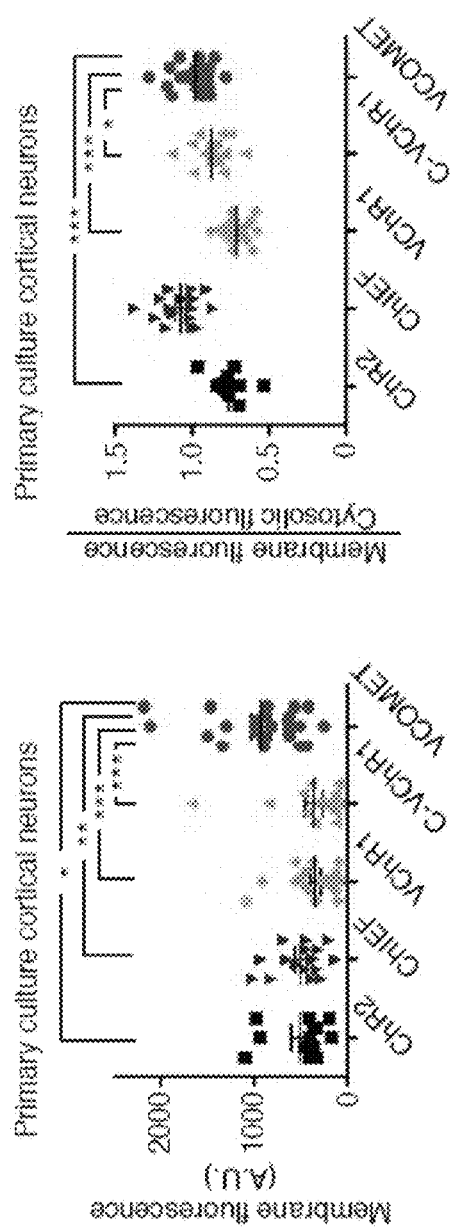
FIG. 7F
FIG. 7G
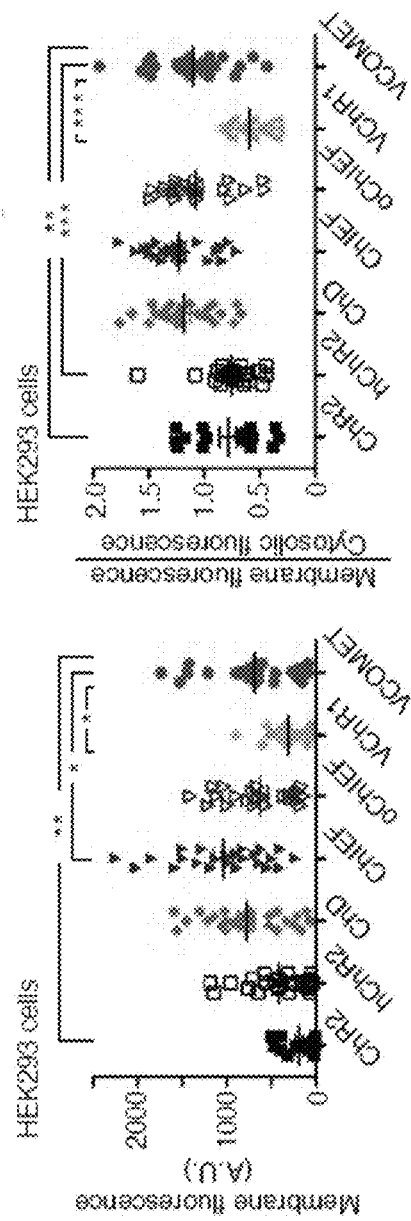
FIG. 7H
FIG. 7I

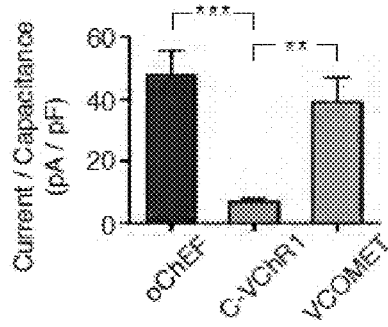 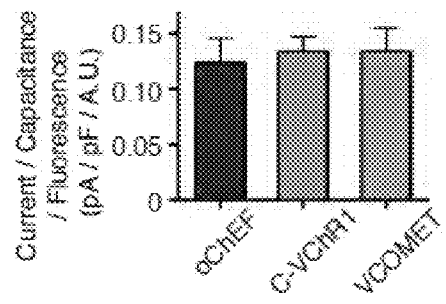
FIG. 8A  FIG. 8B
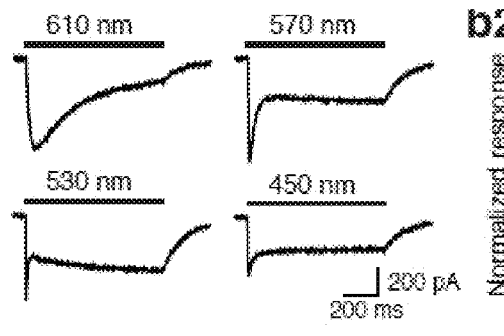 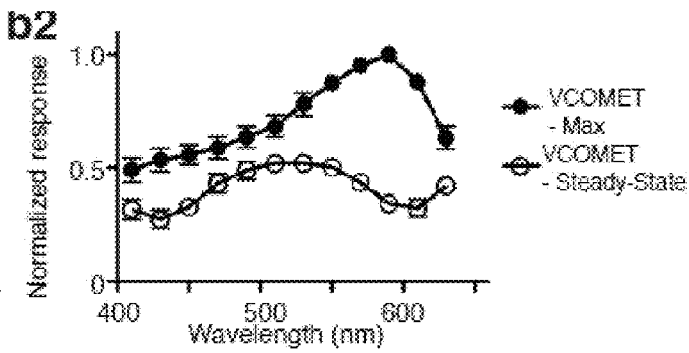
FIG. 8C  FIG. 8D
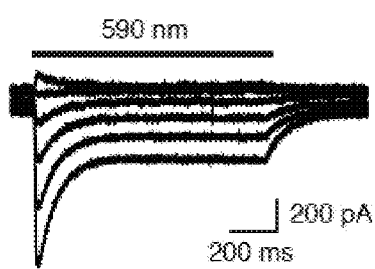 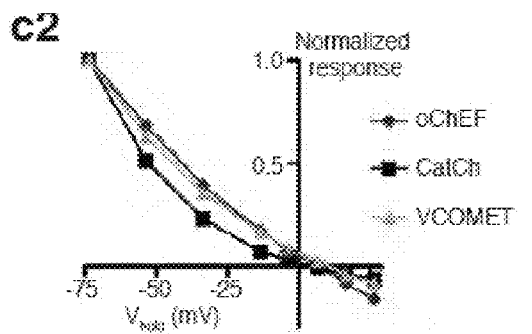
FIG. 8E  FIG. 8F

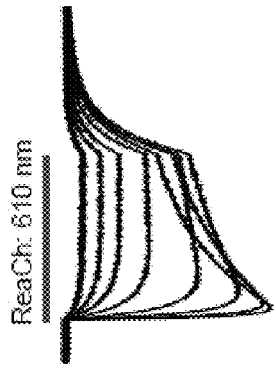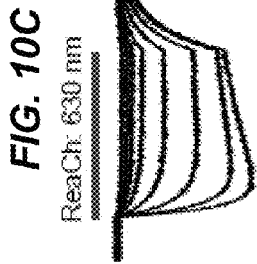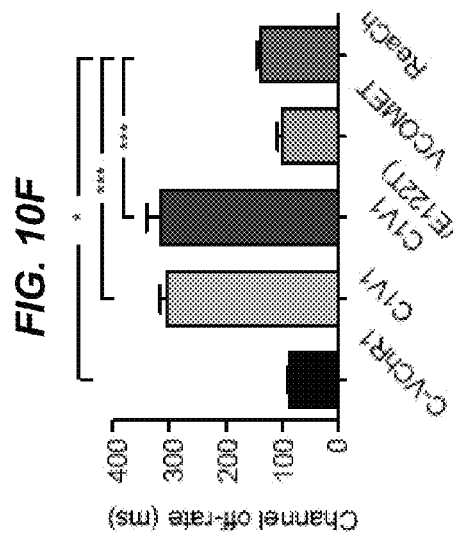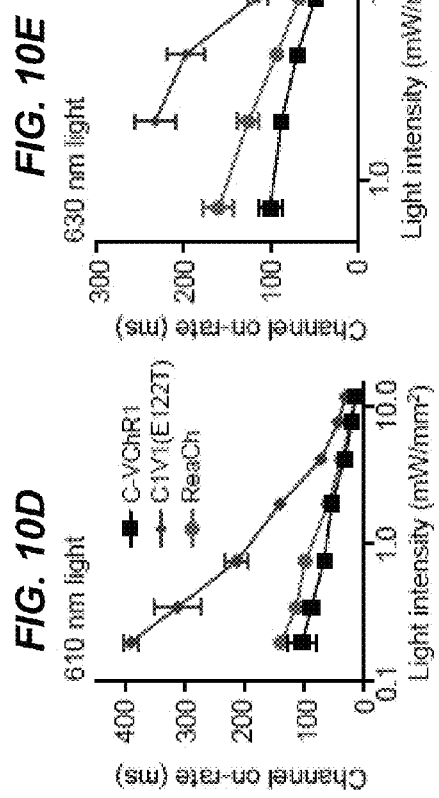

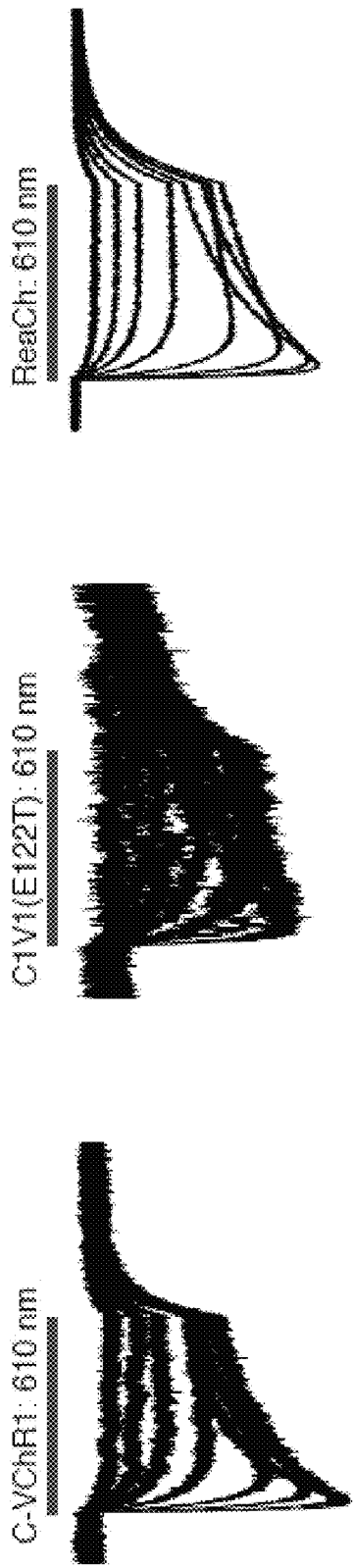
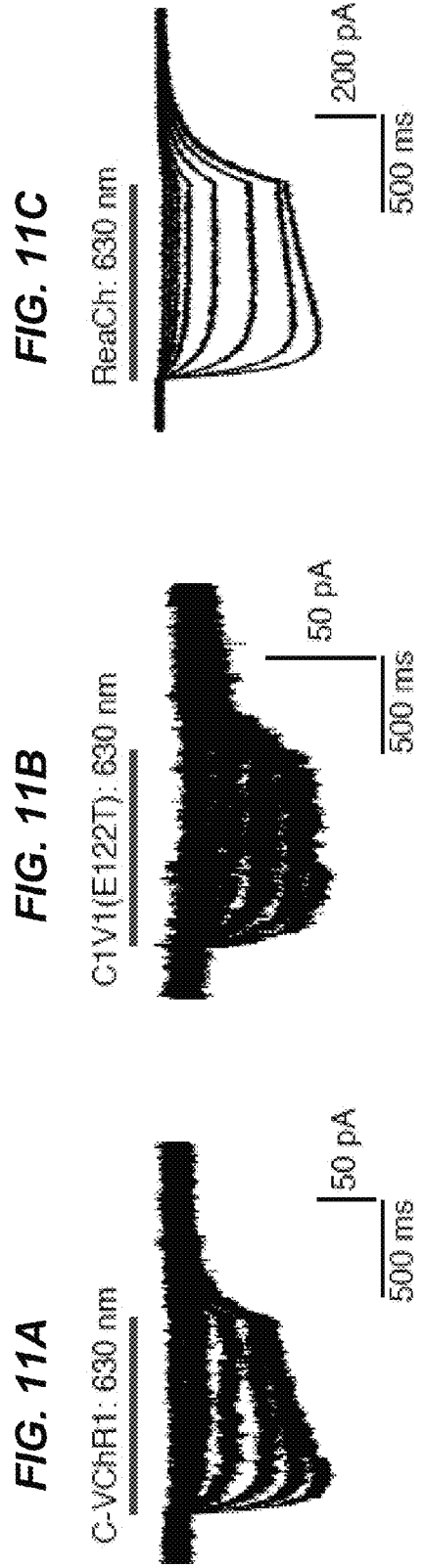

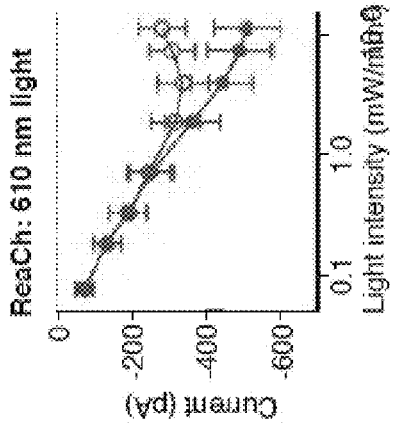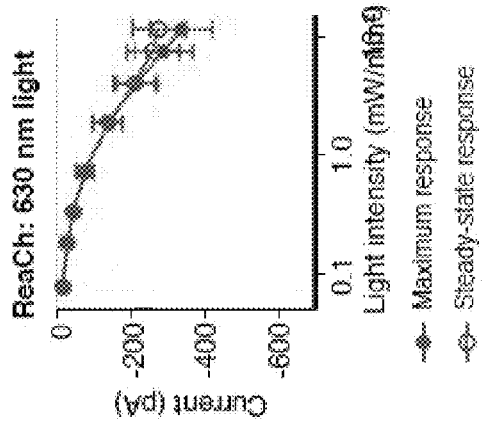
FIG. 11G    FIG. 11H    FIG. 11I
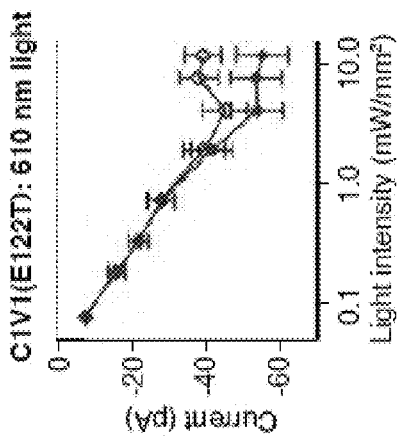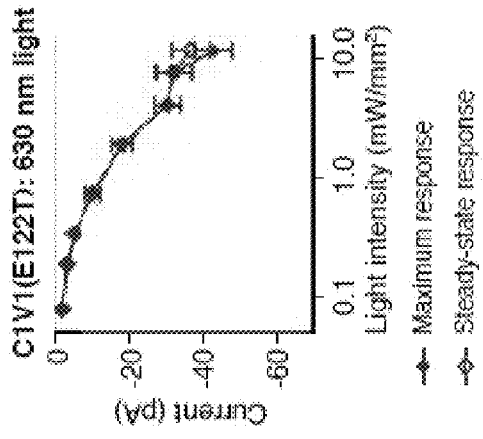
FIG. 11J    FIG. 11K    FIG. 11L

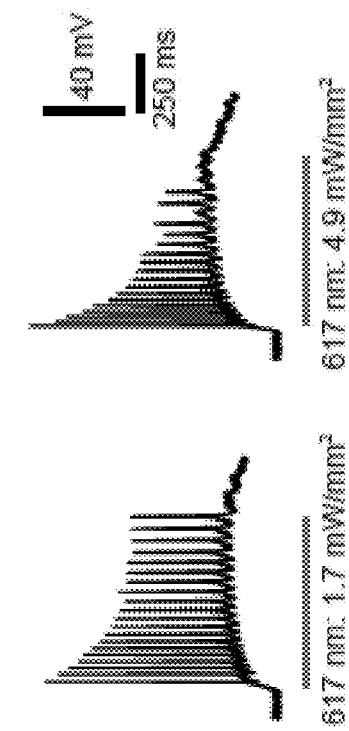
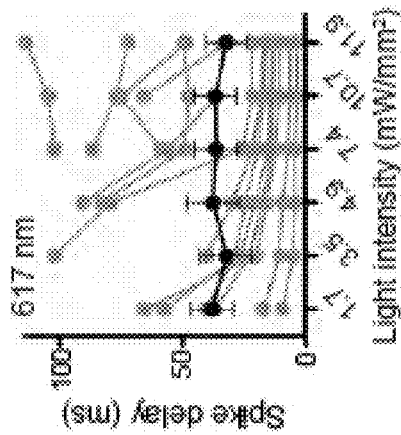
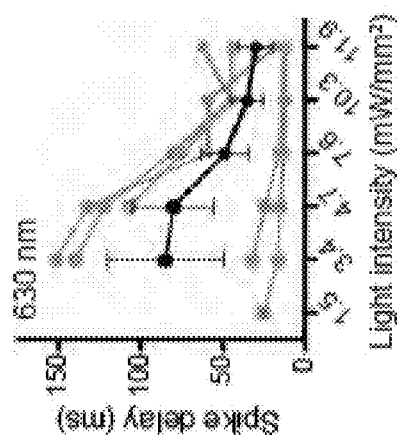
FIG. 12A  FIG. 12B  FIG. 12E  FIG. 12G
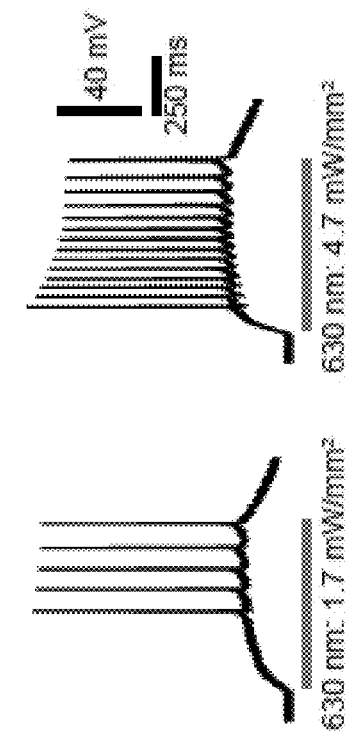
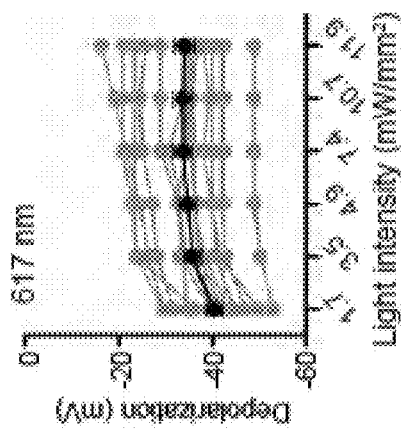
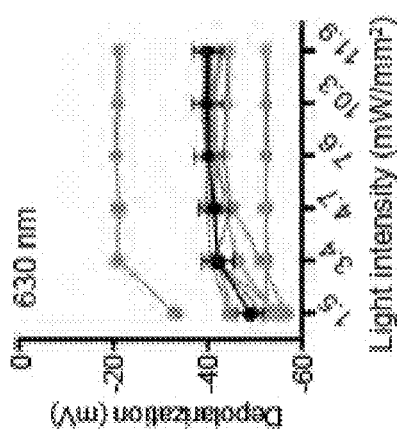
FIG. 12C  FIG. 12D  FIG. 12F  FIG. 12H

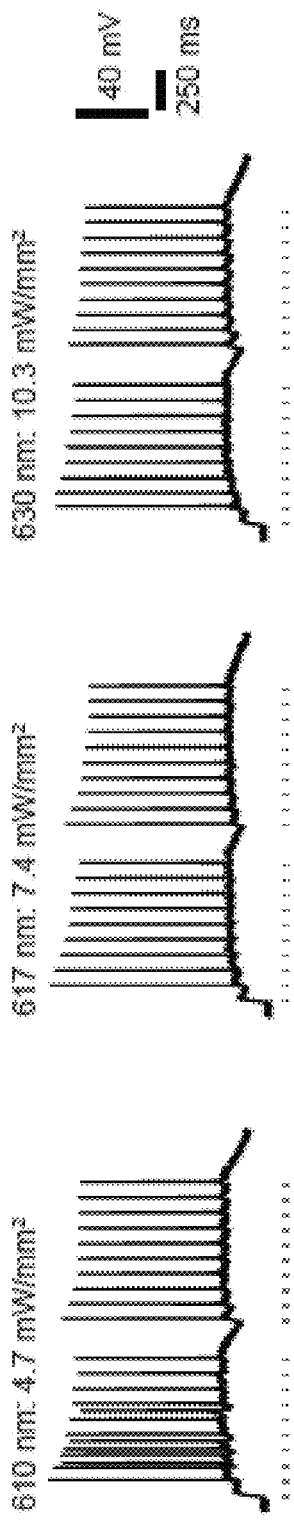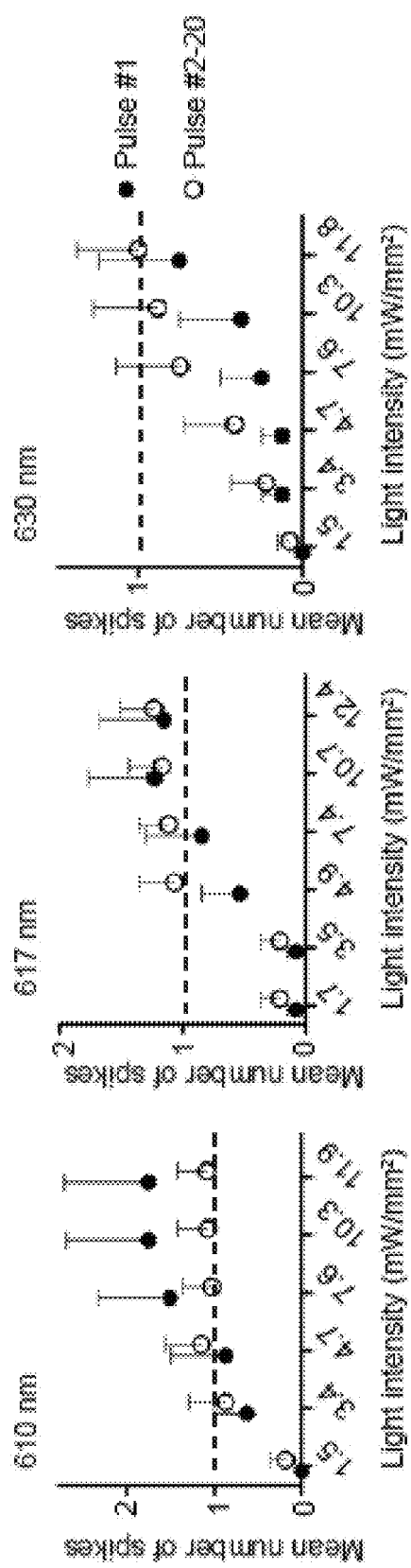

610 nm: 1.7 mW/mm²

610 nm: 4.7 mW/mm²

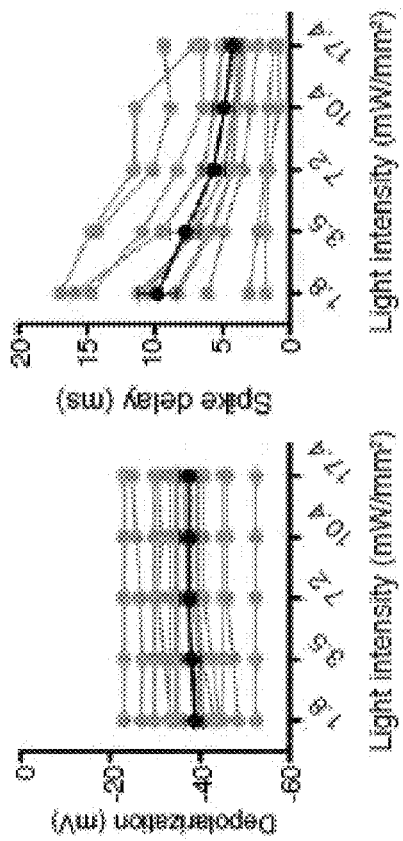 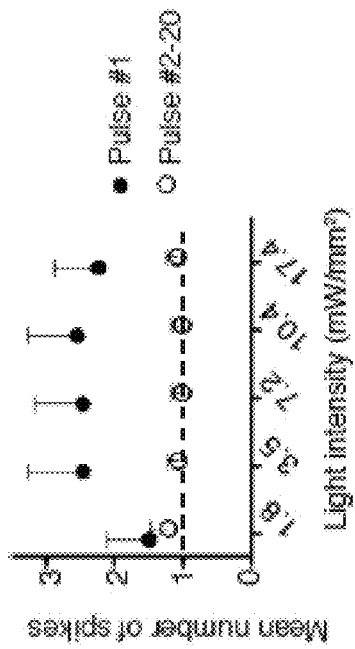 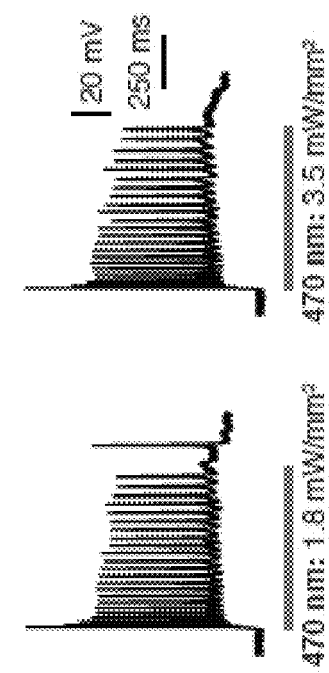 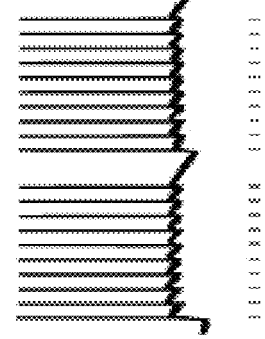
FIG. 14A  FIG. 14B  FIG. 14C  FIG. 14D  FIG. 14E  FIG. 14F

ENGINEERED RED-SHIFTED CHANNELRHODOPSIN VARIANTS

CROSS-REFERENCE TO RELATED APPLICATION

The present application claims the benefit of U.S. Provisional Application No. 61/524,618, filed Aug. 17, 2011, the content of which is expressly incorporated herein by reference in its entirety for all purposes.

GOVERNMENT LICENSE RIGHTS

This invention was made with government support under grant no. NS027177 awarded by the National Institute of Health. The government has certain rights in the invention.

BACKGROUND OF THE INVENTION

Channelrhodopsins (ChR) are light-gated, non-specific cation channels that allow the selective depolarization of genetically targeted cells (Arrenberg, A. B. et al., *Science* 330, 971-974 (2010); Boyden, E. S. et al., *Nat Neurosci* 8, 1263-1268 (2005); Bruegmann, T. et al., *Nat Methods* 7, 897-900 (2010); Nagel, G. et al., *Science* 296, 2395-2398 (2002); Nagel, G. et al., *Proc Natl Acad Sci USA* 100, 13940-13945 (2003); and Adamantidis, A. R. et al., *Nature* 450, 420-424 (2007), the contents of which are hereby expressly incorporated by reference in their entireties for all purposes). As such, channelrhodopsins are used as genetically expressible proteins that are capable of depolarizing genetically selective neurons with high temporal and spatial precision. Currently available ChRs, however, are limited by action spectra that typically peak at 450-545 nm (Lin, J. Y. et al., *Biophys J* 96, 1803-1814 (2009); Wen, L. et al., *PLoS One* September 23; 5(9) (2010); Govorunova, E. G. et al., *MBio.* June 21; 2(3) (2011); Kleinlogel, S. et al., *Nat Neurosci* 14, 513-518 (2011); and Yizhar, O. et al., *Nature* 477, 171-178 (2011), the contents of which are hereby expressly incorporated by reference in their entireties for all purposes).

In mammalian systems, these blue-green lights have limited penetration depths into tissue, as the light of these wavelengths are strongly absorbed by endogenous chromophores such as flavins, hemoglobin, and melanin. Blue-green light is also prone to a higher degree of scattering, as compared to light having longer wavelength, especially when penetrating through nervous tissues (Tromberg, B. J. et al., *Neoplasia* 2, 26-40 (2000)).

To circumvent this problem, one or more thin optical fibers can be inserted into neural tissue for deep ChR excitation (Aravanis, A. M. et al., *J Neural Eng* 4, S143-156 (2007)). Although effective in eliciting ChR activation, such invasive procedures damage neural structures en route to the target, require precise stereotaxic positioning, may become damaged in freely behaving animals, and thus may be difficult to perform when ChR is expressed in deep nuclei, such as in the brainstem of mammals.

A number of channelrhodopsin variants are known in the art. For example, Lin et al. (*Biophys J,* 2009, 96(5): 1803-14) describe making chimeras of the transmembrane domains of ChR1 and ChR2, combined with site-directed mutagenesis. Zhang et al. (*Nat Neurosci,* 2008, 11(6): 631-3) describe VChR1, which is a red-shifted channelrhodopsin variant. VChR1 has lower light sensitivity and poor membrane trafficking and expression. Other known channelrhodopsin variants include ChR2 (Nagel, G., et al., *Proc Natl Acad Sci USA,* 2003, 100(24): 13940-5), ChR2/H134R (Nagel, G., et al., *Curr Biol,* 2005, 15(24): 2279-84), and ChD/ChEF/ChIEF (Lin, J. Y., et al., *Biophys J,* 2009, 96(5): 1803-14), which are activated by blue light (470 nm) but show no sensitivity to orange/red light. Additional variants have been disclosed by Lin (Lin, J. Y., *Experimental Physiology,* 2010, 96.1: 19-25). Knopfel et al. (*The Journal of Neuroscience,* 2010, 30(45): 14998-15004) have reviewed a number of second generation optogenetic tools, including ChR.

SUMMARY OF THE INVENTION

The present disclosure provides solutions to these and other problems by providing red-shifted channelrhodopsins with spectral peaks near or above 600 nm, where light absorption by hemes and scattering drops off steeply (Tromberg, B. J. et al., *Neoplasia* 2, 26-40 (2000)). The red-shifted channelrhodopsins provided herein allow for in vivo stimulation of deep structures with ex vivo light sources. Placement of the light source outside the tissue or region of interests allows a greater volume of effective illumination and reduces invasiveness of the stimulation. Additionally, the present disclosure provides channelrhodopsin variants with improved channel kinetics, allowing for temporally-precise optical activation in the millisecond time scale.

In one aspect, a channelrhodopsin variant, denoted Red-activatable Channelrhodopsin (ReaCh) is provided. Advantageously, ReaCh is optimally excited with orange to red light (λ~590-635 nm) and offers improved membrane trafficking, higher photocurrents, and faster kinetics as compared to existing red-shifted channelrhodopsins. Red light suffers less from tissue scattering and blood absorption than the blue to green wavelengths required by other available channelrhodopsin variants. ReaCh expressed in layer Vb neurons of vibrissa motor cortex in awake mice drove spiking and downstream motor output by exciting through the intact Skull. Furthermore, illumination through the aural canal of ReaCh expressed in motoneurons of the facial nucleus of the brainstem could evoke precise vibrissa movements. Thus ReaCh provides a means for the optical activation of neurons without transcranial windows or optical fibers.

Accordingly, in one aspect, the disclosure provides engineered red-shifted channelrhodopsin variants. In some embodiments, the channelrhodopsin variants are characterized by improved membrane trafficking and expression, unique spectral properties, and/or improved kinetic properties.

In one aspect, the present disclosure provides a polypeptide comprising a channelrhodopsin-1 (ChR1) domain, a *Volvox carteri* channelrhodopsin-1 (VChR1) domain and a *Volvox carteri* channelrhodopsin-2 (VChR2) domain.

In one embodiment of the polypeptides described above, the polypeptide has the structure $X^1$-$X^2$-$X^3$-$X^4$, wherein $X^1$ is a ChR1 domain, $X^2$ is a first VChR1 domain, $X^3$ is a VChR2 domain, and $X^4$ is a second VChR1 domain.

In one embodiment of the polypeptides described above, the polypeptide comprises a sequence according to SEQ ID NO: 1.

In one embodiment of the polypeptides described above, one or more of the domains comprises 1, 2, 3, 4 or 5 amino acid mutations relative to a corresponding wild-type domain.

In one embodiment of the polypeptides described above, the amino acid at one or more positions selected from 163, 171, 174 and 266 is mutated.

In one embodiment of the polypeptides described above, the polypeptide comprises one or more substitutions selected from (a) Glu163Thr, (b) Leu171Ile or Leu171Val, (c) His174Arg and (d) Phe266Tyr.

In one embodiment of the polypeptides described above, the polypeptide further comprising a fluorescent polypeptide.

In one aspect, the present disclosure provides a nucleic acid encoding a polypeptide described above.

In one embodiment of the nucleic acids described above, the nucleic acid comprises a sequence according to SEQ ID NO: 2.

In one aspect, the present disclosure provides a method of depolarizing a cell comprising: expressing the polypeptide of any of claims 1-8 within the cell, and exposing the cell to light.

In one embodiment of the methods described above, the expressing step comprises transfecting the cell with a nucleic acid described above.

In one embodiment of the methods described above, the light has a wavelength of at least about 600 nm.

In one aspect, the present disclosure provides a method of restoring sensitivity to light in an ocular cell comprising expressing the polypeptide of any of claims 1-8 in the ocular cell.

In one aspect, the present disclosure provides a channelrhodopsin variant polypeptide comprising an amino acid sequence that is at least 85% identical to SEQ ID NO:1 [VCOMET]. In one embodiment of the polypeptides described above, the polypeptide comprises an amino acid sequence that is at least 90% identical to SEQ ID NO:1 [VCOMET]. In one embodiment of the polypeptides described above, the polypeptide comprises an amino acid sequence that is at least 95% identical to SEQ ID NO:1 [VCOMET]. In one embodiment of the polypeptides described above, the polypeptide comprises an amino acid sequence of SEQ ID NO:1 [VCOMET].

In one embodiment of the polypeptides described above, the polypeptide comprises further comprising an L171I amino acid substitution [ReaCh].

In one embodiment of the polypeptides described above, the polypeptide comprises an amino acid sequence of SEQ ID NO:4 [ReaCh].

In one embodiment of the polypeptides described above, the channelrhodopsin variant polypeptide provides a photocurrent of at least 10 pA/pF upon photostimulation with light having a wavelength of at least 600 nm in HEK293 cells.

In one embodiment of the polypeptides described above, the ratio of membrane to cytosol localization for a channelrhodopsin variant polypeptide provided herein is at least 1.0, when expressed in an HEK293 cell.

In one embodiment of the polypeptides described above, the polypeptide further comprises a fluorescent protein fused to the C-terminus.

In one aspect, the present disclosure provides a polynucleotide encoding a channelrhodopsin variant polypeptide as described above.

In one embodiment of the polynucleotides described above, the polynucleotide is a mammalian expression vector. In one embodiment of the polynucleotides described above, the mammalian expression vector is a recombinant adeno-associated viral vector (rAAV).

In one aspect, the present disclosure provides a method for achieving suprathreshold excitation in a neuron, the method comprising: expressing a channelrhodopsin variant polypeptide described herein in the neuron, and exposing the cell to light comprising a wavelength between 580 nm and 700 nm.

In one embodiment of the methods described above, expressing the polypeptide comprises transfecting the cell with a polynucleotide described above.

In one embodiment of the methods described above, the light comprises a wavelength between 600 nm and 660 nm. In one embodiment of the methods described above, the light comprises a wavelength between 600 nm and 630 nm.

In one embodiment of the methods described above, the cell is exposed to a pulse of light having a frequency between 5 and 50 Hz.

In one embodiment of the methods described above, the cell is exposed to one or more pulses of light lasting from 100 ms to 2,000 ms. In one embodiment of the methods described above, the light pulse lasts from 500 ms to 1,000 ms.

In one embodiment of the methods described above, the neuron is present in the brain of a mammal. In one embodiment of the methods described above, the mammal is a rodent. In one embodiment of the methods described above, the mammal is a human.

In one aspect, the present disclosure provides a method for stimulating a deep brain structure in a mammal, comprising: transfecting a cell within the brain of the mammal with a polynucleotide described above, and shining a light on the exterior of the head of the mammal, the light comprising a wavelength from 580 nm to 680 nm.

In one embodiment of the methods described above, transfecting a cell with the brain of the mammal comprises intercranial injection of the polynucleotide.

In one embodiment of the methods described above, the light comprises a wavelength between 600 nm and 660 nm. In one embodiment of the methods described above, the light comprises a wavelength between 600 nm and 630 nm.

In one embodiment of the methods described above, the method comprises shining the light into the ear of the mammal.

In one embodiment of the methods described above, the mammal is a rodent.

In one embodiment of the methods described above, the mammal is a human.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2A-D show the response of VCOMET, VCOMET-L171I, and VChR1 to long wavelength visible light. (A) Response of VCOMET (grey) and VCOMET-L171I (black) to long wavelength visible light of 570 nm, 590 nm, 610 nm, and 630 nm. (B) Response spectra of VCOMET-L171I (●) and VChR1 (◆), normalized to the maximal response of the cell at the same photon flux. ss indicates the steady-state response measured 700-750 ms after the onset of illumination. * indicates significance level of at least 5%. Relative desensitization of VCOMET-L171I (●) and VChR1 (♦) photo-response at the indicated light intensities in response to 610 nm (C) and 630 nm (D) light, quantitated as the amplitude 900-1000 ms after illumination normalized to the maximal response at the indicated light intensity. * indicates significance level of at least 5%.

FIG. 3A-F show the induction of action potentials in cultured cortical neurons expressing VCOMET-Leu171Ile with 610 nm (A-C) and 630 nm (D-F) light. (A) An example of 610 nm light-induced super-threshold depolarization in cortical neurons leading to action potential firing. (B) Light intensity required to achieve super-threshold depolarization in VCOMET-Leu171Ile expressing neurons in response to illumination with 610 nm light. (C) The spike delay of VCOMET-Leu171Ile expressing neuron in response to illumination with 610 nm light of increasing intensity. (D) An example of 630 nm light-induced super-threshold depolarization in cortical neurons leading to action potential firing. (E) Light intensity required to achieve super-threshold depolarization in VCOMET-Leu171Ile expressing neurons in response to illumination with 630 nm light. (F) The spike delay of VCOMET-Leu171Ile expressing neuron in response to illumination with 630 nm light of increasing intensity.

FIG. 5 provides an amino acid sequence (SEQ ID NO:1) of an engineered red-shifted ehannelrhodopsin polypeptide, according to one embodiment. Also shown is polynucleotide sequence (SEQ ID NO:2) encoding the polypeptide. The origin of various domains of the engineered polypeptide are indicated with highlighting: green =ChIEF/ChR1; purple =VChR1; red =VChR2; and blue =Kozak sequence.

FIG. 6 provides a biophysical characterization of the channelrhodopsin variant ReaCh, as compared to C-VChR1 and C1V1(E122T). (A) The schematic of the design of ReaCh variant. ReaCh contains the N-terminal of the ChEF/ChIEF variant, transmembrane domains A-E and G of VChR1, transmembrane domain F of VChR2, and an L171I point mutation in transmembrane domain C. (B) Typical examples of C1V1 (E122T) and ReaCh expression as visualized with mCitrine fluorescence. ReaCh expression in HEK293 cells is mainly membrane-localized as visualized by mCitrine fluorescence. In comparison, C1V1(E122T) expression is localized at both the membrane and cytosol, with strong intracellular aggregation. The relative membrane expression level (C) and membrane/cytosol fluorescence ratio (D) of VChR1, C-VChR1, C1V1, C1V1(E122T), and ReaCh, as measured with mCitrine fluorescence. (E) The mean photocurrent amplitudes of C-VChR1, C1V1, C1V1(E122T), VCOMET, and ReaCh recorded from HEK293 cells. The current amplitudes were measured at the wavelengths that evoked the greatest response of each variant and normalized to cell capacitance. (F) The response of C-VChR1 (top row), C1V1(E122T) (middle row), and ReaCh (bottom row) to 650, 630, 610, 590, 470 and 410 nm light of same photon flux. The spectra of the maximum response (G) and steady-state/plateau response (H) of C-VChR1 (n=7), C1V1(E122T) (n=8) and ReaCh (n=7). Statistical tests were performed on all pairs of variants, but only significant differences with ReaCh are shown on the graph. * indicates $p \leq 0.05$,  indicates $p \leq 0.01$, and * indicates $p \leq 0.001$.

FIG. 8 provides a biophysical characterization of the red-shifted channelrhodopsin variant VCOMET. (A) Comparisons of the mean photocurrent amplitudes of mammalian codon optimized ChEF (oChEF), C-VChR1, and VCOMET in randomly selected expressing HEK293 cells showing the significant smaller photocurrent of C-VChR1. (B) The photocurrent amplitudes in (A) normalized to the membrane fluorescence of each cells showing similar photocurrent when normalized to expression level. The mean oChEF response is measured with 470 nm light illumination. C-VChR1 and VCOMET responses are measured with 570 nm light illumination. (C) Representative current traces of VCOMET in response to light stimulation of the indicated wavelength. (D) The response spectra of VCOMET (n=7). Solid circle indicated the maximum obtainable response at each wavelength and empty circle indicated the steady-state response measured between 700-750 ms after the onset of light pulses. (E) Representative current responses of VCOMET at different holding potential. (F) The mean current-voltage relationship of VCOMET compared to the ChR2 variant CatCh and oChEF. Note the reduced rectification with oChEF and VCOMET. * indicates $p \leq 0.05$,  indicates $p \leq 0.01$, and * indicates $p \leq 0.001$. Statistical tests for (A) conducted with one way ANOVA followed by Tukey's test between all pairs of columns.

FIG. 10 provides a comparison of the kinetics of C-VChR1, C1V1(E122T) and ReaCh. Representative responses of C-VChR1 (A), C1V1(E122T) (B) and ReaCh (C) expressed in HEK293 cell to 0.08, 0.19, 0.34, 0.74, 1.93, 4.09, 7.65 and 11.75 mW/mm$^2$ of 610 nm light. (D-F) the same cells in (A-C) responding to 630 nm light of 0.08, 0.19, 0.34, 0.73, 1.92, 4.07, 7.61 and 11.69 mW/mm2. The channel onset time constants of C-VChR1 (n=10), C1V1(E122T) (n=6) and ReaCh (n=10) to 610 nm (G) and 630 nm (H) light of different intensities. (I) The channel closure time constants of C-VChR1 (n=11), C1V1 (n=6), C1V1(E122T) (n=8), VCOMET (n=9) and ReaCh (n=11). Although statistic comparisons were made between all pairs of variants, only the significant differences to ReaCh are shown on the graph. * indicates $p \leq 0.05$,  indicates $p \leq 0.01$, and * indicates $p \leq 0.001$.

FIG. 11 shows the light-intensity-current amplitude relationships of C-VChR1, C1V1(E122T) and ReaCh. (A-F) The same traces shown in FIG. 10A-F are shown with C-VChR1 and C1V1(E122T) response curves displayed using a smaller scale. (G-L) Summary of the light intensity-current amplitude relationship of C-VChR1 (G and J) (n=10), C1V1 (E122T) (n=6) (H and K) and ReaCh (n=10) (I and L) to 610 nm (c) and 630 nm (d) light, respectively.

FIG. 12 shows light-induced depolarization in primary culture hippocampal neurons expressing ReaCh. Representative traces of the current-clamp recording of a primary cultured hippocampal neuron in response to 750 ms of 617 nm light at 1.7 mW/mm$^2$ (A) and 4.9 mW/mm$^2$ (B) and 630 nm light at 1.7 mW/mm$^2$ (C) and 4.7 mW/mm$^2$ (D). The levels of depolarization in response to 617 nm (E; n=16) and 630 nm (F; n=8) light of different light intensities. The spike delay of ReaCh expressing cells in response to 617 nm (G) and 630 nm (H) light of different light intensities. The mean depolarization and spike delay in (E-F) and (G-H), respectfully, are indicated by the black symbols and lines and the individual cell responses are indicated by gray lines (n=16 for 617 nm light and n=8 for 630 nm light). The representative responses of cultured hippocampal neurons expressing ReaCh responding to 10 Hz light stimulation of 610 nm (I), 617 nm (J) and 630 nm (K) light. Summaries of the mean number of spikes evoked by the first light pulse (solid circle) and pulse 2-20 at different light intensities with 610 nm (L; n=8), 617 nm (M; n=13) and 630 nm (N; n=8) light. 10 Hz light pulses were gated by a mechanical shutter at 5 ms (610 nm) or 10 ms (617 or 630 nm) pulse duration.

FIG. 14 shows the response of ReaCh-expressing primary culture hippocampal neurons to 470 nm stimulation. (A) Representative membrane traces of a ReaCh-expressing neuron exposed to 750 ms of 470 nm light at 1.8 mW/mm$^2$ (A) and 3.5 mW/mm$^2$ (B). (C) The level of membrane depolarization obtained by stimulation of ReaCh using 470 nm light of increasing intensities in ReaCh-expressing neurons. (D) The delay of the light-induced action potential of ReaCh when stimulated with 470 nm light of increasing intensities in ReaCh-expressing neurons. (E) Representative traces of membrane depolarization and action potentials of ReaCh expressed in neurons when triggered by pulsed 470 nm light (5 ms duration with mechanical shutter) at 10 Hz. (F) The mean number of action potentials (spikes) triggered by the first light pulse (filled circles) and 2nd-20th pulses (open circles) as shown in (E), averaged from 13 cells.

DETAILED DESCRIPTION OF THE INVENTION

Introduction

Figure 1A:
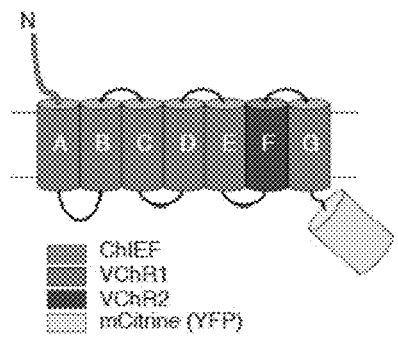
FIG. 1A-E provides a characterization of an engineered red-shifted channelrhodopsin variant tagged with a fluorescent protein, according to one embodiment. (A) A schematic illustration of mCitrine-tagged VCOMET, containing an N-terminal sequence from ChIEF, transmembrane domains A-E and G from VChR1, and transmembrane domain F from VChR2. The VCOMET protein shown in FIG. 1A is further fused to mCitrine, a YFP variant fluorescent protein. (B) Representative fluorescent images of VChR1-mCitrine (left panel) and VCOMET-mCitrine (right panel) expressed in cultured neurons. (C) Quantification of VCOMET (●), ChR2 (■), and VChR1 (◆) membrane trafficking determined as the ratio of membrane fluorescence to total cellular fluorescence. (D) Response of VCOMET and VChR1 to light of varying wavelengths from 410 nm to 610 nm. (E) Maximum (Max; filled shapes) and steady-state (SS; open shapes) response spectra of VCOMET (▼), ChIEF (■), and VChR1 (◆).

The optimal wavelength for optical imaging into mammalian tissue is between 600 nm to 1300 nm, where the light scattering decreases with increasing wavelength and absorption by enodogenous chromophores is reduced. This allows for the deeper penetration of light into tissue with reduced attenuation (Tromberg, B. J. et al., *Neoplasia* 2, 26-40 (2000)). Utilization of optogenetic tools to manipulate neuronal activity would have the same wavelength dependence.

Current development of channelrhodopsins has produced many variants (e.g., ChR2/H134R, ChETA, TC, SFO/D156A, ChD, oChEF, oChIEF, CatCh and ChRGR) that are maximally activated by blue and green lights (Lin, J. Y. et al., *Biophys J* 96, 1803-1814 (2009); Wen, L. et al., *PLoS One* September 23; 5(9) (2010); Kleinlogel, S. et al., *Nat Neurosci* 14, 513-518 (2011); Nagel, G. et al., *Curr Biol* 15, 2279-2284 (2005); Gunaydin, L. A. et al., *Nat Neurosci* 13, 387-392 (2010); Berndt, A. et al., *Nat Neurosci* 12, 229-234 (2009); and Berndt, A. et al., *Proc Natl Acad Sci USA* 108, 7595-7600 (2011), the contents of which are hereby expressly incorporated herein by reference in their entireties for all purposes). Many of these variants have improved properties regarding to the kinetics, expression and level of desensitization. However, there has been very little progress in the development of red-shifted channelrhodopsins.

Among other embodiments, the present disclosure provides two such red-shifted channelrhodopsins, VCOMET and ReaCh, which display strong membrane expression in mammalian cells. Advantageously, the ReaCh variant responds strongly to light above 600 nm, and has spectral peaks for transient and steady responses at 590 nm and 630 nm, respectively. The latter compares favorably with the 620 nm absorbance peak of the longest wavelength visual pigment yet found in nature, cyanopsin (Liebman, P. & Entine, G., *Nature* 216, 501-503 (1967); and Hubbard, R. et al., *Methods in Enzymology*, Vol. 18C. (eds. D. B. McCormick & L. D. Wright) 615-653 (Academic Press, New York; 1971)). The cyanopsin chromophore is 11-cis-3-dehydroretinal, which differs from all-trans retinal in the algal channels by an extra double bond in the ionone ring and cis stereochemistry at one double bond in the polyene chain. These two alterations would be expected to shift the absorbance peak to longer and shorter wavelengths, respectively. Even longer wavelength absorbance peaks, up to 830 nm, have been observed when bacteriorhodopsin is reconstituted with azulenic analogs of retinal, but these chromophores are highly unnatural and the resulting proteins do not undergo normal photocycles (Bell, J. R. et al., *J Phys Chem A* 102, 5481-5483 (1998)).

As shown herein, the spectral advantages of ReaCh allow efficient activation of expressing neurons through intact tissue in adult mice with red-orange (617 nm) and red (627 nm) light. The recently published channelrhodopsin variant C1V1, and its derivatives, were reported to have improved expression and membrane trafficking and kinetic properties compared to VChR1 (Yizhar, O. et al., *Nature* 477, 171-178 (2011)). However, as shown herein, C1V1 and its variants are still limited in their membrane trafficking compared to VCOMET and ReaCh, in addition to having channel kinetics that are approximately 3 times slower than VCOMET and ReaCh. The most red-shifted C1V1 derivative C1V1(E122T) has a spectral peak at approximately 600 nm, although the E122T mutation reduces the C1V1 photocurrent approximately 3-fold, in addition to having slow channel kinetics. The reduction of photocurrent by E122T in C1V1 is consistent with what has previously been reported (Yizhar, O. et al., *Nature* 477, 171-178 (2011).

The reduction of photocurrent from this single mutation may result from the position of this residue at the putative channel pore of ChR as predicted from the recently published crystal structure of channelrhodopsin ChEF (Kato, H. E. et al. *Nature* January 22; 482(7385):369-74 (2012), the content of which is expressly incorporated by reference herein for all purposes). The reduction of C1V1(E122T) photocurrent and slow kinetics negate the spectral advantage that the E122T mutation provides. It is possible to over-express the channel and utilize additional trafficking signal to 'increase' the photo-responses at longer wavelength as previously shown (Yizhar, O. et al., *Nature* 477, 171-178 (2011); Gradinaru, V. et al., *Cell* 141, 154-165 (2010), the contents of which are hereby expressly incorporated by reference in their entireties for all purposes), although the reliability and safety of such strategy is not known, as several groups have reported increased toxicity when using this strategy.

Advantageously, it was not necessary to use these strategies with ReaCh to achieve depolarization with red light. Rather, suprathreshold depolarization was achieved in ReaCh-expressing neurons with 610 nm light even at low intensities. As predicted, the ability to trigger temporally-precise spiking with channelrhodopsins depends on the expression level of the protein in addition to the other factors such as membrane properties of the expressing cells and channel kinetics (Lin, J. Y., *Exp Physiol* 96, 19-25 (2011), the content of which is expressly incorporated by reference herein in its entirety for all purposes). However, using the red-shifted channelrhodopsin variants provided here, specific selection of cells with high expression levels was not needed to stimulate with light, nor was selection for the results from one particular cell type in the culture. These results therefore closely represent what users of this channelrhodopsin will encounter when utilized in vivo, where the expression level varies from cell to cell and decreases from the site of viral injection. Regardless of these variations, ReaCh can be used reliably to trigger temporally-precise spiking in vivo through intact tissue.

Definitions

The articles "a," "an" and "the" as used herein do not exclude a plural number of the referent, unless context clearly dictates otherwise. The conjunction "or" is not mutually exclusive, unless context clearly dictates otherwise. The term "include" refers to non-exhaustive examples.

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present invention, the following terms are defined.

Although the length of channelrhodopsin proteins vary in nature, it was previously characterized that the N-terminal 300 to 400 amino acids, which consist of an N-terminal domain and seven transmembrane helices, are sufficient for normal photocurrent functionality. Accordingly, in some embodiments, a "channelrhodopsin polypeptide" refers to a polypeptide comprising the N-terminal 300-400 amino acids of a naturally occurring channelrhodopsin protein, chimera, or variant thereof, having photocurrent activity. In some embodiments, a channelrhodopsin polypeptide refers to a polypeptide comprising the N-terminal domain and seven transmembrane domains of one or more naturally occurring channelrhodopsin proteins, a chimera, or variant thereof.

The term "corresponding residue" refers to an amino acid in a first channelrhodopsin variant polypeptide which is analogous (e.g., structurally or functionally equivalent) or homologous (e.g., evolutionarily conserved in the primary amino acid sequence) with an amino acid in a second channelrhodopsin variant polypeptide or reference channelrhodopsin polypeptide, whether or not the amino acid numbers of the first and second channelrhodopsin polypeptides align (e.g., corresponding residue 174 in a first channelrhodopsin polypeptide may be residue 164 in a second channelrhodopsin polypeptide).

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a channelrhodopsin variant polypeptide of the invention linked to a fluorescent protein or fragment thereof.

The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the pre-sequence of subunit IV of cytochrome c oxidase (see, also, Hancock et al., *EMBO J.* 10:4033-4039, 1991; Buss et al., *Mol. Cell. Biol.* 8:3960-3963, 1988; U.S. Pat. No. 5,776,689, each of which is incorporated herein by reference).

The term "operatively linked" or "operably linked" or "operatively joined" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a channelrhodopsin variant polypeptide described herein can be fused to a fluorescent protein or fragment thereof. In this case, it is preferable that the fusion molecule retains its potential to generate photocurrent and ability to achieve suprathreshold excitement of neurons, and the fluorescent protein or fragment thereof retains its fluorescence. In some embodiments of the present invention, the activities of either the channelrhodopsin variant polypeptide or the fluorescent protein can be reduced relative to their activities in isolation. Such fusions can also find use with the present invention.

The term "polypeptide" or "protein" refers to a polymer of four or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "wild-type" or "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "non-naturally occurring" is used to refer to a protein, nucleic acid molecule, cell, or other material that does not occur in nature. For example, the channelrhodopsin variant polypeptide and fusion proteins thereof provided by the present invention are non-naturally occurring because they consist of domains from multiple natural channelrhodopsin proteins and/or contain amino acid variations not found in the corresponding naturally-occurring protein in nature.

The term "identical," when used in reference to two or more polynucleotide sequences or two or more polypeptide sequences, refers to the residues in the sequences that are the same when aligned for maximum correspondence. When percentage of sequence identity is used-in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any-well known algorithm (see, for example, Meyers and Miller, Comp. Appl. Biol. Sci. 4:11-17, 1988; Smith and Waterman, Adv. Appl. Math. 2:482, 1981; Needleman and Wunsch, J. Mol. Biol. 48:443, 1970; Pearson and Lipman, Proc. Natl. Acad. Sci., USA 85:2444 (1988); Higgins and Sharp, Gene 73:237-244, 1988; Higgins and Sharp, CABIOS 5:151-153; 1989; Corpet et al., Nucl. Acids Res. 16:10881-10890, 1988; Huang, et al., Comp. Appl. Biol. Sci. 8:155-165, 1992; Pearson et al., Meth. Mol. Biol., 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid.

As to amino acid sequences, one of skill will recognize that individual substitutions, deletions or additions to a nucleic acid, peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Conservative amino acid substitutions providing functionally similar amino acids are well known in the art. Dependent on the functionality of the particular amino acid, i.e., catalytically important, structurally important, sterically important, different groupings of amino acid may be considered conservative substitutions for each other. Table 1 provides groupings of amino acids that are considered conservative substitutions based on the charge and polarity of the amino acid, the hydrophobicity of the amino acid, the surface exposure/structural nature of the amino acid, and the secondary structure propensity of the amino acid.

TABLE 1

Groupings of conservative amino acid substitutions based on the functionality of the residue in the protein.

| Important Feature | Conservative Groupings |
|---|---|
| Charge/Polarity | 1. H, R, and K |
| | 2. D and E |
| | 3. C, T, S, G, N, Q, and Y |
| | 4. A, P, M, L, I, V, F, and W |
| Hydrophobicity | 1. D, E, N, Q, R, and K |
| | 2. C, S, T, P, G, H, and Y |
| | 3. A, M, I, L, V, F, and W |
| Structural/Surface Exposure | 1. D, E, N, Q, H, R, and K |
| | 2. C, S, T, P, A, G, W, and Y |
| | 3. M, I, L, V, and F |
| Secondary Structure Propensity | 1. A, E, Q, H, K, M, L, and R |
| | 2. C, T, I, V, F, Y, and W |
| | 3. S, G, P, D, and N |
| Evolutionary Conservation | 1. D and E |
| | 2. H, K, and R |
| | 3. N and Q |
| | 4. S and T |
| | 5. L, I, and V |
| | 6. F, Y, and W |
| | 7. A and G |
| | 8. M and C |

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity. In certain embodiments, substantially similar sequences will have at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature, under defined ionic strength and pH, at which 50% of the target sequence hybridizes to a perfectly matched probe.

The term "allelic variants" refers to polymorphic forms of a gene at a particular genetic locus, as well as cDNAs derived from mRNA transcripts of the genes, and the polypeptides encoded by them. The term "preferred mammalian codon" refers to the subset. of codons from among the set of codons encoding an amino acid that are most frequently used in proteins expressed in mammalian cells as chosen from the following list: Gly (GGC, GGG); Glu (GAG); Asp (GAC); Val (GUG, GUC); Ala (GCC, GCU); Ser (AGC, UCC); Lys (AAG); Asn (AAC); Met (AUG); Ile (AUC); Thr (ACC); Trp (UGG); Cys (UGC); Tyr (UAU, UAC); Leu (CUG); Phe (UUC); Arg (CGC, AGG, AGA); Gln (CAG); His (CAC); and Pro (CCC).

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of the present invention. In general, a fluorescent protein useful for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of *Aequorea* GFP can be derived from the naturally occurring GFP by engineering mutations such as amino acid substitutions into the reference GFP protein.

Many cnidarians use green fluorescent proteins as energy transfer acceptors in bioluminescence. The term "green fluorescent protein" is used broadly herein to refer to a protein that fluoresces green light, for example, *Aequorea* GFP. GFPs have been isolated from the Pacific Northwest jellyfish, *Aequorea victoria*, the sea pansy, *Renilla reniformis*, and *Phialidium gregarium* (Ward et al., *Photochem. Photobiol.* 35:803-808, 1982; Levine et al., *Comp. Biochem. Physiol.* 72B:77-85, 1982, each of which is incorporated herein by reference). Similarly, reference is made herein to "red fluorescent proteins", which fluoresce red, "cyan fluorescent proteins," which fluoresce cyan, and the like. RFPs, for example, have been isolated from the corallimorph *Discosoma* (Matz et al., *Nature Biotechnology* 17:969-973 [1999]). The term "red fluorescent protein," or "RFP" is used in the broadest sense and specifically covers the *Discosoma* RFP (DsRed), and red fluorescent proteins from any other species, such as coral and sea anemone, as well as variants thereof as long as they retain the ability to fluoresce red light.

Channelrhodopsin Variant Polypeptides

In one aspect, the present disclosure provides new channelrhodopsin variants. Rhodopsins are proteins that become depolarized after light activation. They are often used in studies with neurons or are useful when screening certain types of inhibitors that can effect membrane changes in the cell, such as PKC, $Ca^{2+}$, etc. They may be useful in treating certain types of retinal degeneration. Native rhodopsins are sensitive to light wavelengths shorter than some of the compounds disclosed herein, and the sensitivity to longer wavelengths results in improved tissue penetration.

Figure 5:
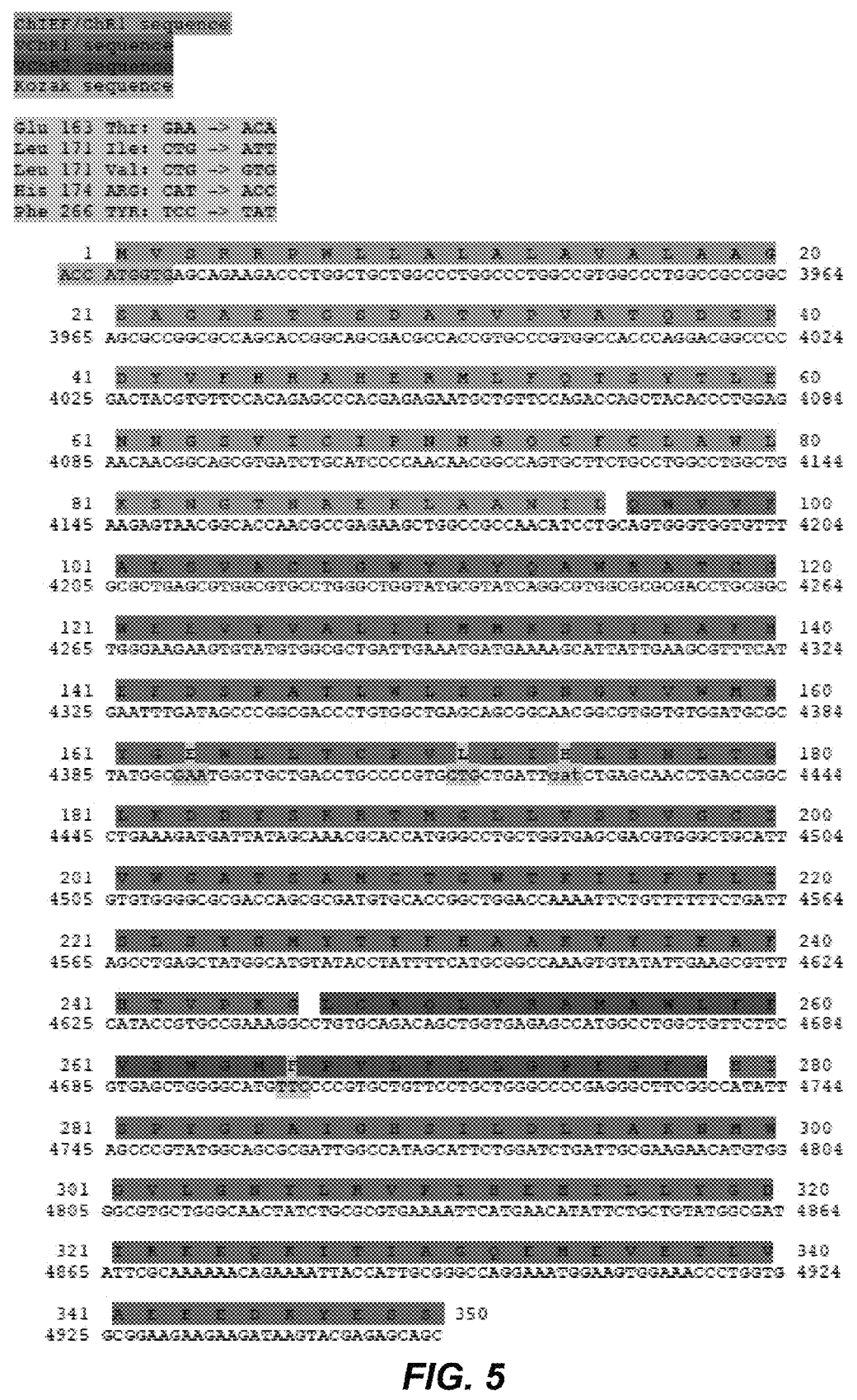
Figure 17:
FIG. 17 provides an amino acid sequence (SEQ ID NO:4) of an engineered red-shifted channelrhodopsin polypeptide, according to one embodiment. Also shown in a polynucleotide sequence (SEQ ID NO:5) encoding the polypeptide. The origin of various domains of the engineered polypeptide are indicated with highlighting: green =ChIEF/ChR1; purple =VChR1; red =VChR2; and blue =Kozak sequence.

In one embodiment, the disclosure provides a channelrhodopsin variant polypeptide comprising an N-terminal domain and seven transmembrane domains, A-G, respectively. In a specific embodiment, the channelrhodopsin variant polypeptide has a domain structure as shown in FIGS. 5 and 17, where: amino acids 3 to 95 correspond to the N-terminal domain (also referred to herein as $X^1$); amino acids 96 to 246 correspond to transmembrane domains A to E (also referred to herein as $X^2$); amino acids 247 to 278 correspond to transmembrane domain F (also referred to herein as $X^3$); and amino acids 279 to 350 correspond to transmembrane domain G and optionally additional C-terminal sequence (also referred to herein as $X^4$).

In certain embodiments, additional amino acids may be appended to the N-terminus and/or C-terminus of the channelrhodopsin variant polypeptide without affecting the global structure and function of core domains $X^1$-$X^2$-$X^3$-$X^4$.

In one embodiment, the N-terminal domain ($X^1$) of a channelrhodopsin variant provided herein comprises from 80 to 110 amino acids of the ChIEF/ChR1 N-terminal domain sequence. In a specific embodiment, the N-terminal domain ($X^1$) of a channelrhodopsin variant provided herein consists of from 93 to 95 amino acids of the ChIEF/ChR1 N-terminal domain sequence and optionally additional residues at the N-terminus. In one embodiment, the N-terminal domain is at least 85% identical to the N-terminal 80 to 110, preferably N-terminal 93 to 95, amino acids of ChIEF/ChR1. In yet other embodiments, the N-terminal domain is at least 86%, 87%, 88%, 89%, 90%, 91%, 92%, 93%, 94%, 95%, 96%, 97%, 98%, 99% or 100% identical to the N-terminal 80 to 110, preferably N-terminal 93 to 95, amino acids of ChIEF/ChR1. In one embodiment, the N-terminal domain shares homology with the N-terminal 95 amino acids of ChIEF/ChR1. In yet other embodiments, the N-terminal domain shares homology with the N-terminal 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 amino acids of ChIEF/ChR1.

In one embodiment, transmembrane domains A to E ($X^2$) of a channelrhodopsin variant provided herein consist of transmembrane domains A to E of VChR1. In one embodiment, transmembrane domains A to E have an amino acid sequence that is at least 85% identical to the amino acid sequence of transmembrane domains A to E of VChR1. In yet other embodiments, transmembrane domains A to E have an amino acid sequence that is at least 86%, 87%, 88%, 89%, 90%, 91%, 92%, 93%, 94%, 95%, 96%, 97%, 98%, 99%, or 100% identical to the amino acid sequence of transmembrane domains A to E of VChR1.

In one embodiment, transmembrane domain F ($X^3$) of a channelrhodopsin variant provided herein consists of transmembrane domain F of VChR2. In one embodiment, transmembrane domain F has an amino acid sequence that is at least 85% identical to the amino acid sequence of transmembrane domain F of VChR2. In yet other embodiments, transmembrane domain F has an amino acid sequence that is at least 86%, 87%, 88%, 89%, 90%, 91%, 92%, 93%, 94%, 95%, 96%, 97%, 98%, 99%, or 100% identical to the amino acid sequence of transmembrane domain F of VChR2.

In one embodiment, transmembrane domain G ($X^4$) of a channelrhodopsin variant provided herein consists of transmembrane domain F of VChR1. In one embodiment, transmembrane domain G has an amino acid sequence that is at least 85% identical to the amino acid sequence of transmembrane domain F of VChR1. In yet other embodiments, transmembrane domain G has an amino acid sequence that is at least 86%, 87%, 88%, 89%, 90%, 91%, 92%, 93%, 94%, 95%, 96%, 97%, 98%, 99%, or 100% identical to the amino acid sequence of transmembrane domain F of VChR1.

In one embodiment, a channelrhodopsin variant polypeptide provided herein comprises an amino acid sequence that is at least 85% identical to SEQ ID NO:1 [VCOMET], over the entire length of SEQ ID NO:1. In another embodiment, a channelrhodopsin variant polypeptide provided herein comprises an amino acid sequence that is at least 90% identical to SEQ ID NO:1 [VCOMET], over the entire length of SEQ ID NO:1. In another embodiment, a channelrhodopsin variant polypeptide provided herein comprises an amino acid sequence that is at least 95% identical to SEQ ID NO:1 [VCOMET], over the entire length of SEQ ID NO:1. In other embodiments, a channelrhodopsin variant polypeptide provided herein comprises an amino acid sequence that is at least 80, 81, 82, 83, 84, 85, 86, 87, 88, 89, 90, 91, 92, 93, 94, 95, 96, 97, 98, 99, or 100% identical to SEQ ID NO:1 [VCOMET], over the entire length of SEQ ID NO:1.

In one embodiment, a channelrhodopsin variant polypeptide provided herein comprises an amino acid sequence that is at least 85% identical to SEQ ID NO:4 [ReaCh], over the entire length of SEQ ID NO:4, In another embodiment, a charmelrhodopsin variant polypeptide provided herein comprises an amino acid sequence that is at least 90% identical to SEQ ID NO:4 [ReaCh], over the entire length of SEQ ID NO:4, In another embodiment, a chartnelrhodopsin variant polypeptide provided herein comprises an amino acid sequence that is at least 95% identical to SEQ ID NO:4 [ReaCh], over the entire length of SEQ ID NO:4, In other embodiments, a charmelrhodopsin variant polypeptide provided herein comprises an amino acid sequence that is at least 80, 81, 82, 83, 84, 85, 86, 87, 88, 89, 90, 91, 92, 93, 94, 95, 96, 97, 98, 99, or 100% identical to SEQ ID NO:4 [ReaCh], over the entire length of SEQ ID NO:4.

Advantageously, the channelrhodopsin variant polypeptides provided herein produce a higher photocurrent upon photoactivation with orange, orange-red, and red light, as compared to naturally occurring channelrhodopsin proteins and other red-shifted variants described to date. Accordingly, in one embodiment, a channelrhodopsin variant polypeptide provided herein provides a photocurrent of at least 10 pA/pF upon photostimulation with light having a wavelength of at least 580 nm, preferably at least 600 nm, in HEK293 cells. In other embodiments, a channelrhodopsin variant polypeptide provided herein provides a photocurrent of at least 11 pA/pF, 12 pA/pF, 13 pA/pF, 14 pA/pF, 15 pA/pF, 16 pA/pF, 17 pA/pF, 18 pA/pF, 19 pA/pF, 20 pA/pF, 21 pA/pF, 22 pA/pF, 23 pA/pF, 24 pA/pF, 25 pA/pF, 26 pA/pF, 27 pA/pF, 28 pA/pF, 29 pA/pF, 30 pA/pF, 31 pA/pF, 32 pA/pF, 33 pA/pF, 34 pA/pF, 35 pA/pF, 36 pA/pF, 37 pA/pF, 38 pA/pF, 39 pA/pF, 40 pA/pF, or greater photocurrent upon photostimulation with light having a wavelength of at least 580 nm, preferably at least 600 nm in HEK293 cells. In one embodiment, photocurrent is measured after photostimulation with 610 nm, 617 nm, 630, or 655 nm light. In another embodiment, the photocurrent is measured after stimulation with light having a wavelength from 580 nm to 680 nm, 600 nm to 660 nm, or 600 nm to 630 nm.

Advantageously, the channelrhodopsin variant polypeptides provided herein traffic more efficiently to the cellular membrane, as compared to other red-shifted variants described to date. Accordingly, in one embodiment, the ratio of membrane to cytosol localization, as measured by fluorescence of a fluorescent protein fused to the C-terminus, for a channelrhodopsin variant polypeptide provided herein is at least 1.0. In other embodiments, ratio of membrane to cytosol localization for a channelrhodopsin variant polypeptide provided herein is at least 1.01, 1.02, 1.03, 1.04, 1.05, 1.05, 1.06, 1.07, 1.08, 1.09, 1.1, 1.11, 1.12, 1.13, 1.14, 1.15, or higher.

VCOMET (VChR Optimized for Membrane Expression and Trafficking) is a chimera channelrhodopsin containing components of VChR1, ChR1 and VChR2, in addition to the inclusion of a Kozak sequence. This variant has improved membrane trafficking and increased expression level that gives stronger light-induced response compared to VChR1 when expressed in mammalian cells or neurons but has identical spectral response to VChR1. This variant also has strong activation by orange and red light (wavelength >600 nm) not achievable with the existing ChR2 based variant or ChD/ChEF/ChIEF (Lin, J. Y., et al., Biophys J, 2009, 96(5): 1803-14, the content of which is hereby expressly incorporated by reference in its entirety for all purposes). VCOMET(L171I) has further improved spectral response to light above 600 nm and reduced desensitization to 610 and 630 nm light, resulting in more consistent responses to these wavelengths of light compared to VChR1. VCOMET(L171I, H174R, F266Y) has reduced kinetics, as compared to VCOMET, but increased light sensitivity, resulting in efficient and prolonged opening of the channel when stimulated with 630 nm light. Another variation of VCOMET, incorporating E163T and L171V mutations, has a spectral peak at 550 nm but improved kinetic properties, which allow for more precise temporal control of light-induced depolarization by 570 nm light, as compared to the slow kinetics of VChR1.

Thus, one of the advantages of the variants is that in some embodiments, they may be useful for investigating membrane trafficking by activation with longer wavelengths than previously described variants. Various embodiments provided herein can be used to excite neurons during the study of neuronal circuitry, can restore vision at various wavelengths, and can activate certain voltage gated ion channels.

In one aspect, the disclosure provides a polypeptide comprising or consisting of a combination of domains from any number of channelrhodopsins known in the art. In exemplary embodiments, the polypeptide comprises a channelrhodopsin-1 (ChR1) domain, a *Volvox carteri* channelrhodopsin-1 (VChR1) domain, and a *Volvox carteri* channelrhodopsin-2 (VChR2) domain. A domain from ChIEF (Lin, J. Y., et al., Biophys J, 2009, 96(5): 1803-14) can also be used. Thus, in some embodiments, the polypeptide comprises a ChIEF domain, a VChR1 domain and a VChR2 domain.

In exemplary embodiments, the polypeptide comprises or consists of VCOMET (VChR Optimized for Membrane Expression and Trafficking), which is a chimera of 3 channelrhodopsin variants, encoded by a nucleic acid with an incorporated Kozak sequence. In some embodiments, VCOMET has the following structure: ChR1 (1-95), VChR1 (96-246), VChR2 (247-278), VChR1 (279-350), with amino acid residue #2 coming from the introduced Kozak sequence. That is, in some embodiments, amino acids 1-95 are a sequence derived from ChR1, amino acids 96-246 are a sequence derived from VChR1, amino acids 247-278 are a sequence derived from VChR2, amino acids 279-350 are a sequence derived from VChR1. Thus, VCOMET is a polypeptide comprising multiple domains derived from various channelrhodopsins, for example, contiguous subsequences of various channelrhodopsins. The leading ChR1 sequence improves membrane trafficking of the VCOMET, the VChR2 and Kozak sequence component increases the expression level in mammalian cells (FIG. 1).

In some embodiments, the disclosure provides polypeptide variants, such as a VCOMET variant. A "polypeptide variant" or a "variant" has the sequence of a parent polypeptide that has been varied by one or more amino acid mutations (e.g., deletion, insertion or substitution in any combination). In some embodiments, a polypeptide variant is characterized by 1, 2, 3, 4, 5, 6, 7, 8, 9, 10, or more mutations, as compared to a parent polypeptide. In some embodiments, a polypeptide variant is characterized by 1, 2, 3, 4, 5, 6, 7, 8, 9, 10, or more substitutions, as compared to a parent polypeptide. In some embodiments, a polypeptide variant is characterized by 1, 2, 3 or 4 substitutions, as compared to a parent polypeptide.

The Leu171Ile mutation in VCOMET improves the response to light above 600 nm by creating a secondary peak in the spectral response at 630 nm. The Leu171Ile mutation also reduced the level of desensitization to light above 600 nm, leading to more consistent responses when stimulated by light above 600 nm. Leu171Ile with His174Arg and Phe266Tyr increases the light sensitivity of the channel but also slows the off-rate kinetics of the channel to 630 nm light (channel closure rate constant ~5 s), leading to prolong activation of the channel when single stimulation light pulse. VCOMET with Glu163Thr and Leu171Val mutations have spectral peak at 550 nm but increased kinetic properties (channel off-rate ~16 ms) that has faster termination of the response after illumination.

In exemplary embodiments, a polypeptide comprises or consists of the sequence:

(SEQ ID NO: 1)
```
M V S R R P W L L A L A L A V A L A A G
S A G A S T G S D A T V P V A T Q D G P
D Y V F H R A H E R M L F Q T S Y T L E
N N G S V I C I P N N G Q C F C L A W L
K S N G T N A E K L A A N I L Q W V V F
A L S V A C L G W Y A Y Q A W R A T C G
W E E V Y V A L I E M M K S I I E A F H
E F D S P A T L W L S S G N G V V W M R
Y G E W L L T C P V L L I H L S N L T G
L K D D Y S K R T M G L L V S D V G C I
V W G A T S A M C T G W T K I L F F L I
S L S Y G M Y T Y F H A A K V Y I E A F
```

-continued
```
H T V P K G L C R Q L V R A M A W L F F
V S W G M F P V L F L L G P E G F G H I
S P Y G S A I G H S I L D L I A K N M W
G V L G N Y L R V K I H E H I L L Y G D
I R K K Q K I T I A G Q E M E V E T L V
A E E E D K Y E S S
```

In SEQ ID NO: 1, the sequence at positions 1-95 is a ChIEF/ChR1 domain sequence; the sequence at positions 96-246 is a VChR1 domain sequence; the sequence at positions 247-278 is a VChR2 domain sequence and the sequence at positions 279-350 is also a VChR1 domain sequence.

In some embodiments, a polypeptide comprises or consists of SEQ ID NO: 1 characterized by a mutation, for example, an amino acid substitution. In exemplary embodiments, a polypeptide comprises or consists of SEQ ID NO: 1 characterized by one or more substitutions selected from (a) Glu163Thr, (b) Leu171Ile or Leu171Val, (c) His174Arg, and (d) Phe266Tyr.

In some embodiments, a polypeptide further comprises a fluorescent polypeptide. Any art known fluorescent polypeptide may be suitable, including but not limited to mPlum, mCherry, tdTomato, mStrawberry, J-Red, DsRed-monomer, mOrange, mKO, mCitrine, Venus, Ypet, EYFP, Emerald, EGFP, CyPet, mCFPm, Cerulean and T-Sapphire. See, Shaner et al., Nature Methods, 2005, 2: 905, the content of which is hereby expressly incorporated by reference in its entirety for all purposes. In exemplary embodiments, the fluorescent polypeptide is mCitrine.

In some embodiments, a nucleic acid comprises or consists of the sequence:

(SEQ ID NO: 2)
```
ACCATGGTGAGCAGAAGACCCTGGCTGCTGGCCCTGGCCCTGGCCGTGGCCCTGGCCGCCGGC
AGCGCCGGCGCCAGCACCGGCAGCGACGCCACCGTGCCCGTGGCCACCCAGGACGGCCCC
GACTACGTGTTCCACAGAGCCCACGAGAGAATGCTGTTCCAGACCAGCTACACCCTGGAG
AACAACGGCAGCGTGATCTGCATCCCCAACAACGGCCAGTGCTTCTGCCTGGCCTGGCTG
AAGAGTAACGGCACCAACGCCGAGAAGCTGGCCGCCAACATCCTGCAGTGGGTGGTGTTT
GCGCTGAGCGTGGCGTGCCTGGGCTGGTATGCGTATCAGGCGTGGCGCGCGACCTGCGGC
TGGGAAGAAGTGTATGTGGCGCTGATTGAAATGATGAAAAGCATTATTGAAGCGTTTCAT
GAATTTGATAGCCCGGCGACCCTGTGGCTGAGCAGCGGCAACGGCGTGGTGTGGATGCGC
TATGGCGAATGGCTGCTGACCTGCCCCGTGCTGCTGATTcatCTGAGCAACCTGACCGGC
CTGAAAGATGATTATAGCAAACGCACCATGGGCCTGCTGGTGAGCGACGTGGGCTGCATT
GTGTGGGGCGCGACCAGCGCGATGTGCACCGGCTGGACCAAAATTCTGTTTTTTCTGATT
AGCCTGAGCTATGGCATGTATACCTATTTTCATGCGGCCAAAGTGTATATTGAAGCGTTT
CATACCGTGCCGAAAGGCCTGTGCAGACAGCTGGTGAGAGCCATGGCCTGGCTGTTCTTC
GTGAGCTGGGGCATGTTCCCCGTGCTGTTCCTGCTGGGCCCCGAGGGCTTCGGCCATATT
AGCCCGTATGGCAGCGCGATTGGCCATAGCATTCTGGATCTGATTGCGAAGAACATGTGG
GGCGTGCTGGGCAACTATCTGCGCGTGAAAATTCATGAACATATTCTGCTGTATGGCGAT
ATTCGCAAAAAACAGAAAATTACCATTGCGGGCCAGGAAATGGAAGTGGAAACCCTGGTG
GCGGAAGAAGAAGATAAGTACGAGAGCAGC
```

The ACCATGGTG (SEQ ID NO: 3) sequence at positions 1-9 of SEQ ID NO: 2 is a Kozak sequence. In some embodiments, a nucleic acid comprises or consists of SEQ ID NO: 2 encoding for a mutation, for example, an amino acid substitution. In exemplary embodiments, a nucleic acid comprises or consists of SEQ ID NO: 2 encoding one or more amino acid substitutions selected from (a) Glu163Thr (GAA→ACA), (b) Leu171Ile (CTG→ATT) or Leu171Val (CTG→GTG), (c) His174Arg (CAT→ACC), and (d) Phe266Tyr (TCC→TAT).

In one aspect, the present disclosure provides a variant channelrhodopsin, hereinafter referred to as "ReaCh" (Red-activatable Channelrhodopsin). Compared to known red-shifted channelrhodopsins, i.e., VChR114 and C1V1(E122T)

(Yizhar, O. et al., Nature 477, 171-178 (2011)), ReaCh has improved membrane trafficking and expression in mammalian cells, more robust spectral response above 600 nm, and enhanced steady-state response to light with wavelengths longer than 600 nm. When ReaCh was expressed in layer Vb pyramidal neurons of vibrissae motor cortex (vM1) in the mouse, whisker movement was triggered by transcranial illumination using 617 nm and 655 nm light. Expression of ReaCh in the facial nucleus of the brainstem allowed reliable activation of vibrissal motoneurons with wavelengths up to 627 nm through non-invasive placement of a light emitting diode (LED) at the opening of the ear canal. Thus, ReaCh supports effective non-invasive stimulation of deeper brain structures using channelrhodopsin technology.

In exemplary embodiments, a polypeptide comprises or consists of the sequence:

```
                                          (SEQ ID NO: 4)
M V S R R P W L L A L A L A V A L A A G

S A G A S T G S D A T V P V A T Q D G P

D Y V F H R A H E R M L F Q T S Y T L E

N N G S V I C I P N N G Q C F C L A W L

K S N G T N A E K L A A N I L Q W V V F

A L S V A C L G W Y A Y Q A W R A T C G

W E E V Y V A L I E M M K S I I E A F H

E F D S P A T L W L S S G N G V V W M R

Y G E W L L T C P V I L I H L S N L T G

L K D D Y S K R T M G L L V S D V G C I

V W G A T S A M C T G W T K I L F F L I

S L S Y G M Y T Y F H A A K V Y I E A F

H T V P K G L C R Q L V R A M A W L F F

V S W G M F P V L F L L G P E G F G H I

S P Y G S A I G H S I L D L I A K N M W

G V L G N Y L R V K I H E H I L L Y G D

I R K K Q K I T I A G Q E M E V E T L V

A E E E D K Y E S S
```

One of skill in the art will also recognize that conservative and non-conservative substitutions to a channelrhodopsin variant polypeptide embraced by the present disclosure will be well tolerated, especially at residues whose side chains are surface exposed, residues located in loop regions connecting individual secondary structure elements (e.g., α-helices and β-strands or/and sheets), and at residues not evolutionarily conserved (e.g., residues found distal to an active site, residues at the N- and/or C-terminus). The identification of residues at which conservative and non-conservative amino acid substitutions will be well tolerated is aided by the three-dimensional crystal structure of a channelrhodopsin chimera polypeptide between ChR1 and ChR2 from Chlamydomonas reinhardtii (Kato, H. E. et al. Nature January 22; 482(7385): 369-74 (2012), the content of which is hereby expressly incorporated by reference in its entirety for all purposes).

Accordingly, in certain embodiments, a channelrhodopsin variant polypeptide embraced by the present disclosure may include conservative and/or non-conservative amino acid substitutions at up to, for example, 50% of the residues in the parent polypeptide sequence so long as the global structure and function of the polypeptide is largely conserved. In another embodiment, a channelrhodopsin variant polypeptide embraced by the present disclosure may include conservative and/or non-conservative amino acid substitutions at up to 15% (i.e., 85% sequence identity), preferably 10% (i.e., 90% sequence identity), more preferably 5% (i.e., 95% sequence identity) of the residues in the parent polypeptide sequence. In other embodiments, a channelrhodopsin variant polypeptide embraced by the present disclosure may include conservative and/or non-conservative amino acid substitutions at up to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or more of the residues in the parent polypeptide sequence.

Applications

VCOMET and VCOMET variants VCOMET(Leu171Ile), VCOMET(Leu171Ile and His174Arg) or VCOMET (Glu163Thr and Leu171Val) can be used to depolarize membrane potential of expressing cells effectively with light of wavelength from 590 nm to 650 nm (VCOMET, VCOMET+ Leu171Ile, VCOMET+Leu171Ile+His174Arg) or with 550 nm light with improved temporal precision VCOMET (Glu163Thr+Leu171Val). This can be used to excite expressing neurons selectively to study circuitry. This can also be restore vision in specific wavelength spectra in specific forms of retinal blindness. In addition, it can be used to activate voltage-gated ion channels expressed in cells.

Companies performing research requiring transient depolarization of cultured cells may desire to use channelrhodopsin to perform the depolarization with light stimulus. For example, they may perform depolarization while researching the functions of genes of interest in neurons, or they may perform high-throughput cell-based screens for inhibitors of voltage-gated channels or protein activities induced by calcium entry into the cell, such as PKC, CaMKII, Calcinuerin, or NFAT. Channelrhodopsins would allow transient depolarization of large numbers of cells in solution or during flow, conditions incompatible with depolarization by electrodes or ionic changes. Channelrhodopsins also allow depolarization in precise temporal patterns over large numbers of cells without expensive equipment. It can also be used to restore sensitivity to light in specific form of blindness. Our improved channelrhodopsins would allow stimulation to be performed with red/orange light, which has improved tissue penetration and broadening the spectra of the channelrhodopsin available.

The compounds of the invention can be used in basic research but may also have therapeutic qualities.

EXAMPLES

Example 1

Generation of a New Channelrhodopsin Variant

The concept of using chimeragenesis to generate new channelrhodopsin variant was conceived after the initial discovery that VChR1 poorly trafficks to the cell membrane. The chimera was conceived after comparing the membrane trafficking of ChIEF to ChR2 and VChR1. This channelrhodopsin was fused to mCitrine and tested in HEK293 cells and neurons. Improved membrane trafficking was observed as judged by localization of the fluorescence signal and increased response amplitude when conducting electrophysiology assays. The point mutations Leu171 and Glu163 were introduced to improve the kinetics of the channel, as suggested by previous studies in the channelrhodopsin ChEF and ChR2, respectively. The combination of the two mutations was found to increase the speed of termination of the light-induced response according to the electrophysiological assay. The Leu171 mutation alone was found to increase the response of VCOMET to light above 600 nm by reducing desensitization (FIG. 2). The His174Arg mutation was based on the previous study that reduced the desensitization of ChR2, however, in VCOMET, the corresponding mutation of His174Arg increased light sensitivity and reduced channel kinetics with small effects in the amount of desensitization. Addition of Phe266Tyr was based on the previous observation that the same mutation in ChIEF slows the channel kinetics. The incorporation of Leu171Ile, His174Arg and Phe266Tyr was designed to engineer a channel with slow kinetics for persistent opening after illumination with red light.

Example 2

Design and Engineering of a Red-Activatable Channelrhodopsin

To engineer a red-light activated channelrhodopsin, the red-shifted VChR1 channelrhodopsin variant was used as a template (Zhang, F. et al., Nat Neurosci 11, 631-633 (2008), the content of which is hereby expressly incorporated by reference in its entirety for all purposes). VChR1 expresses poorly in mammalian cells and has minimal trafficking to the membrane (Yizhar, O. et al., Nature 477, 171-178 (2011); and Lin, J. Y., Exp Physiol 96, 19-25 (2011)) resulting in small photocurrents, e.g., <50 pA, that cannot be accurately characterized.

To improve membrane trafficking of the engineered channelrhodopsin, the N-terminal sequence prior to the first transmembrane domain of VChR1 was replaced with the corresponding ChIEF sequence, denoted C-VChR1 (FIG. 6A), which improves its membrane trafficking (Lin, J. Y., Exp Physiol 96, 19-25 (2011)) (FIGS. 6B and C). This strategy is based on the superior membrane trafficking of ChIEF in mammalian cells compared to other ChR variants that results in almost exclusive membrane expression with minimal cytosolic aggregation without the need of introducing additional trafficking signals (FIG. 7) (Lin, J. Y., Exp Physiol 96, 19-25 (2011)).

To improve the expression level, the transmembrane domain E of VChR1 was replaced with the corresponding VChR2 helix, a strategy previously shown to increase the expression level of ChR in ChR1/ChR2 chimeras (Wang, H. et al., J Biol Chem. February 27; 284(9) (2008), the content of which is hereby expressly incorporated by reference in its entirety for all purposes). This new variant has red-shifted response spectra similar to C-VChR1, with spectral peaks at 590 nm and 530 nm for maximum and steady-state/plateau response, respectively (FIGS. 8C and D) and expresses strongly in mammalian cells while retaining robust membrane trafficking (FIG. 7) to yield greater photocurrent in HEK293 cells (38.9±7.8 pA/pF, n=13), as compared to C-VChR1 (6.9±1.0 pA/pF, n=13; FIG. 6D) and comparable photocurrent to mammalian-codon optimized ChEF (oChEF; 47.6±7.7 pA/pF, n=12; FIGS. 8A and B) or mammalian-codon optimized ChIEF (oChIEF; 52.0±6.9 pA/pF, n=7).

This variant was named VChR Optimized for Membrane Expression and Trafficking (VCOMET). VCOMET has a reversal potential (11.5±1.6 mV, Mean±S.E.M., n=8) that is not significantly different (p=0.0527) from the blue-light activated ChRs ChIEF (3.6±1.1 mV, n=5) or CatCh (4.7±0.8 mV, n=6) in physiological saline, and reduced inward rectification similar to ChIEF (FIGS. 8E and F) (Lin, J. Y. et al., Biophys J 96, 1803-1814 (2009)).

Figure 9A:
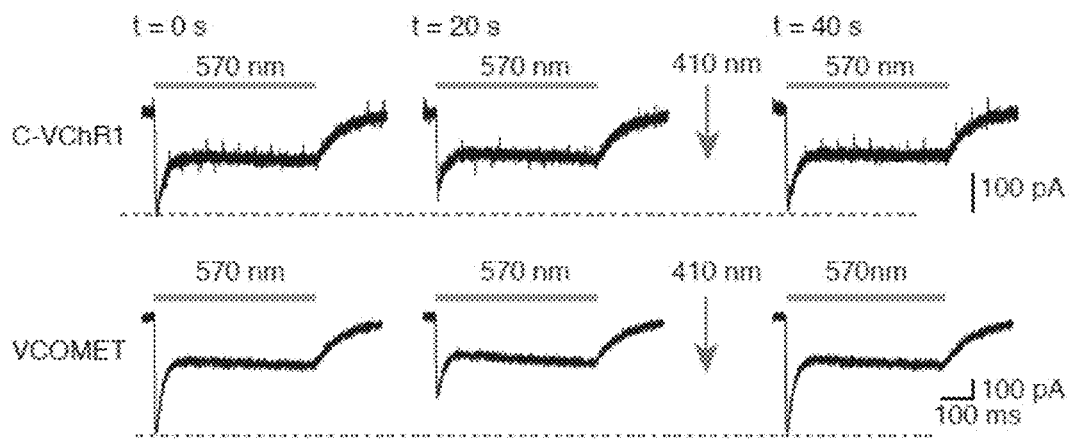
FIG. 9 shows the incomplete recovery of the desensitized responses of C-VChR1, VCOMET and ReaCh. (A) With 2 repetitive stimulations 20 seconds apart, the desensitized transient peak responses of C-VChR1 and VCOMET failed to recover completely in the dark. Preconditioning with 410 nm light enhanced the recovery of the desensitized response in both C-VChR1 and VCOMET. (B) The recovery of the desensitized transient peak response with various second pulse delay, both C-VChR1 and VCOMET failed to reach 100% recovery. (C) The responses of ReaCh to two light pulses 30 seconds apart at the indicated wavelengths. With 570 and 610 nm stimulation, but not with 630 nm, there were a desensitized component that does not recovery fully. (D) Quantification of results shown in (C) with ReaCh and C-VChR1 at the indicated wavelengths.
Figure 9B:
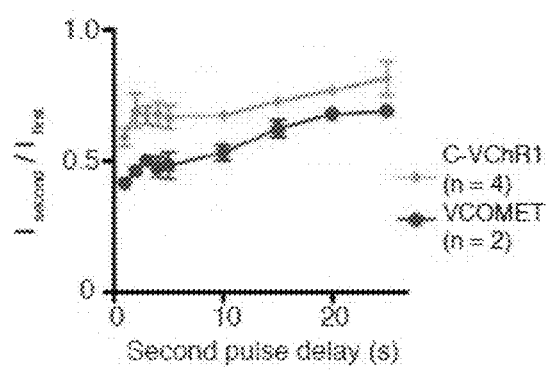
Figure 9C:
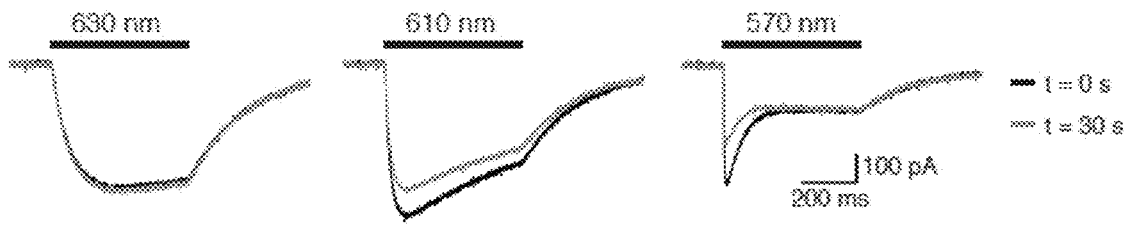
Figure 9D:
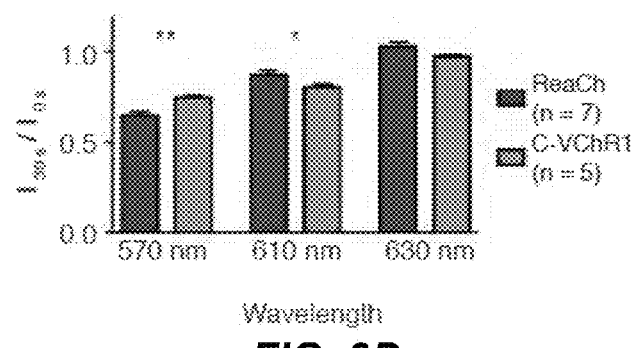
Figure 13A:
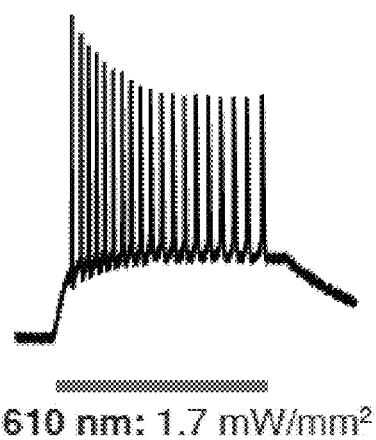
FIG. 13 shows the response of ReaCh-expressing primary culture hippocampal neurons to 610 nm light stimulation. Representative membrane traces of ReaCh-expressing neurons exposed to 750 ms of 610 nm light at 1.7 mW/mm$^2$ (A) and 4.7 mW/mm$^2$ (B). (C) The level of membrane depolarization obtainable by stimulation with 610 nm light of increasing intensities in ReaCh-expressing neurons (n=8). (D) The delay of the light-induced action potential when stimulated with 610 nm light (n=8).
Figure 13B:
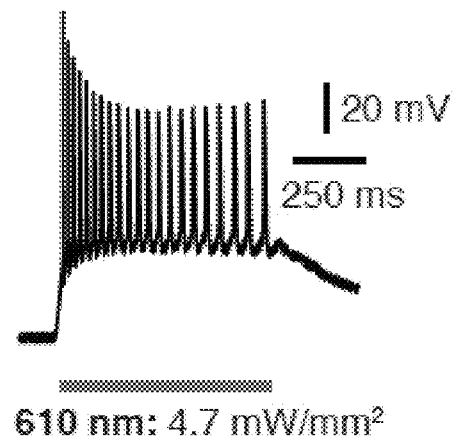
Figure 13C:
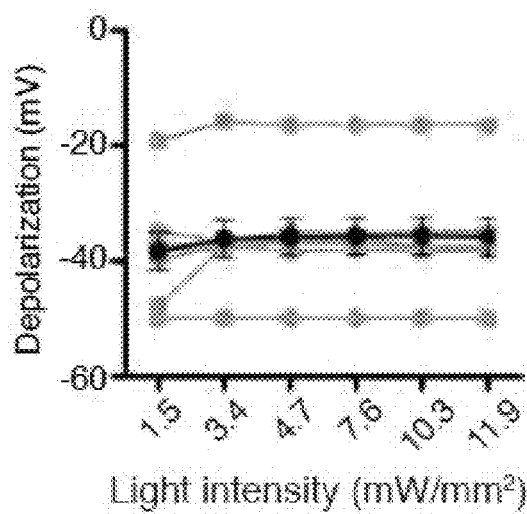
Figure 13D:
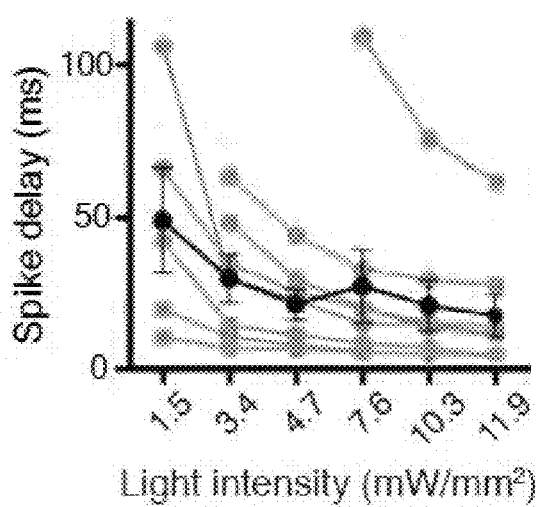

VCOMET responded strongly to light above 600 nm (FIGS. 8C and D), although responses at these longer wavelengths were strongly desensitizing and failed to recover completely in the dark without reconditioning with 410 nm light (FIGS. 9A and B). As most channelrhodopsin experiments utilize the steady-state/plateau photocurrent to achieve suprathreshold excitation of expressing neurons (Nagel, G. et al., Curr Biol 15, 2279-2284 (2005)) and the spectra of the response are commonly defined by the steady-state/plateau spectral peak (Yizhar, O. et al., Nature 477, 171-178 (2011)), the amount of desensitization of VCOMET was reduced using known point mutations of channelrhodopsins.

Figure 1B:
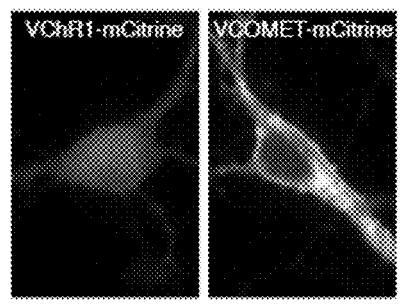
Figure 1C:
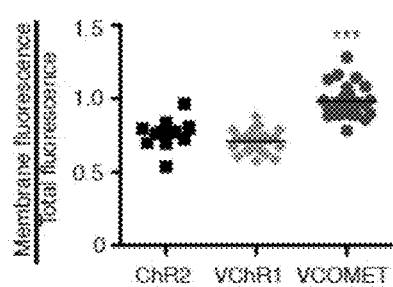
Figure 1D:
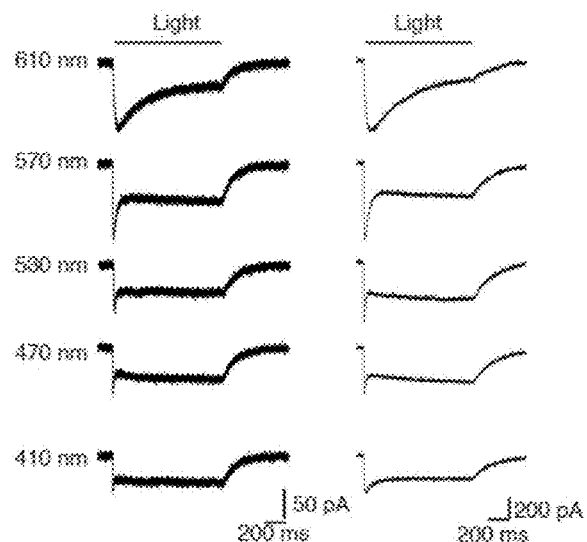
Figure 1E:
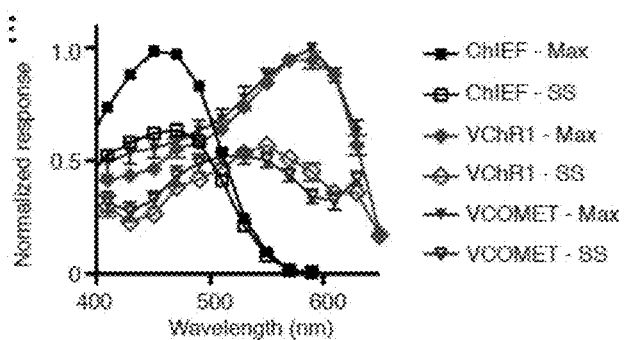
Figure 4A:
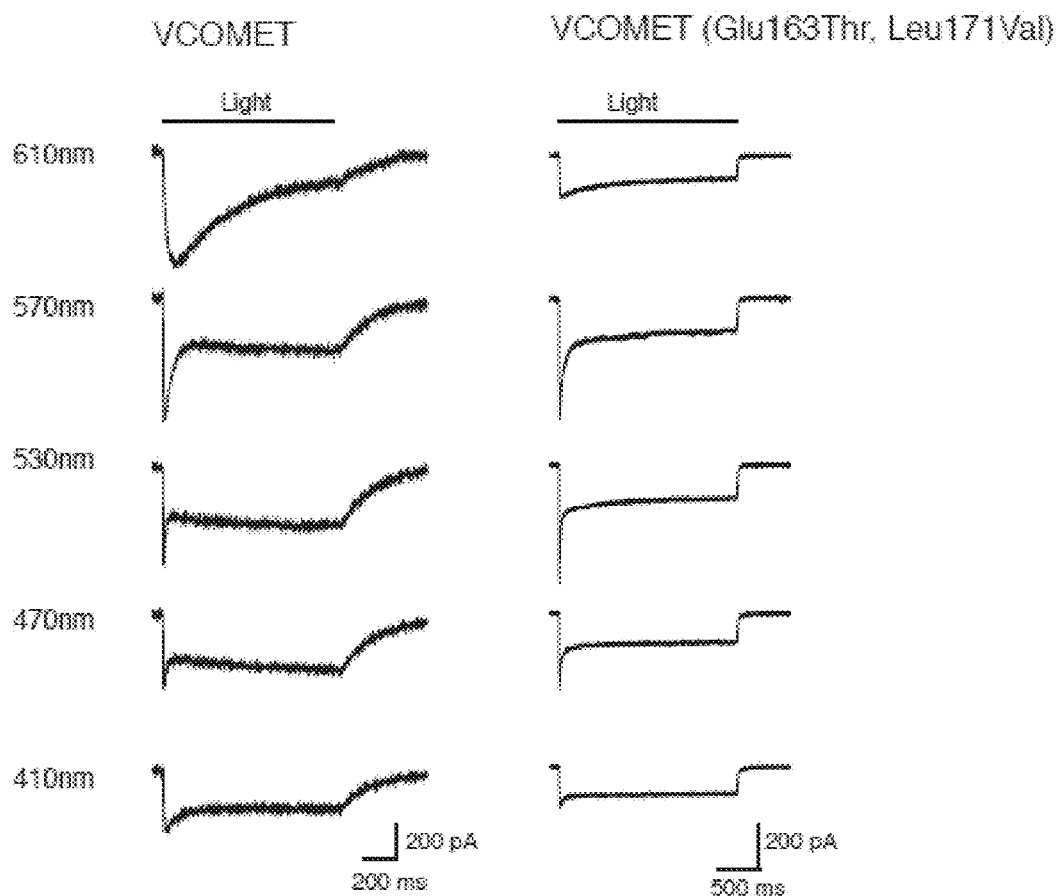
FIG. 4A-B show the response of VCOMET(E163T, L171V) and VCOMET across the visible light spectra. (A) Response of VCOMET (left panel) and VCOMET(E163T, L171V) (right panel) to visible light of 410 nm, 470 nm, 530 nm, 570 nm, and 610 nm. (B) Response spectra of VCOMET (■) and VCOMET(E163T, L171V) (♦), normalized to the maximal response of the cell at the same photon flux.
Figure 4B:
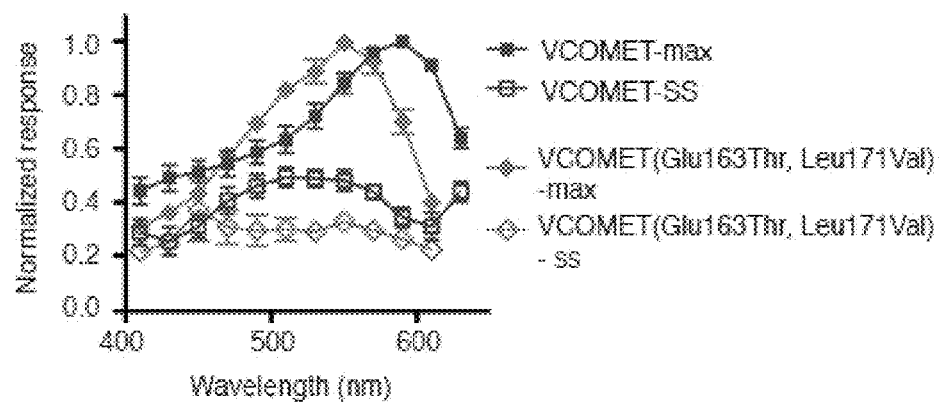
Figure 7A:
FIG. 7 provides a comparison of membrane trafficking and expression level of different channelrhodopsin variants in primary culture cortical neurons and HEK293 cells. Representative fluorescent images of ChR2-mCitrine (A), ChIEF-mCitrine (B), VChR1-mCitrine (C), C-VChR1-mCitrine (D), and VCOMET-mCitrine (E) in primary cortical neurons. Note the ChR2 and ChIEF DNA sequences used native algael codons. (F) Quantification of membrane fluorescence level of different channelrhodopsin variant fused to mCitrine in primary culture neuron. (G) Membrane trafficking of different channelrhodopsin variant fused to mCitrine in primary culture neuron as measured by membrane fluorescence/cytosol fluorescence ratio. (H, I) Identical analysis as (F, G) in HEK293 cells with additional variants of human codon optimized ChR2 (hChR2), ChR1 and ChR2 chimera ChD and mammalian codon optimized ChIEF (oChIEF). * indicates $p \leq 0.05$,  indicates $p \leq 0.01$, and * indicates $p \leq 0.001$. Statistical tests were conducted with one-way ANOVA followed by Tukey's test for all pairs of columns. Despite that statistical tests were done on all pairs of columns, only statistical differences between VCOMET and the compared ChR variants are indicated on the graphs.
Figure 7B:
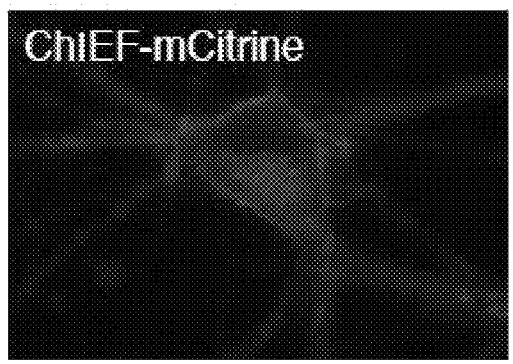
Figure 7C:
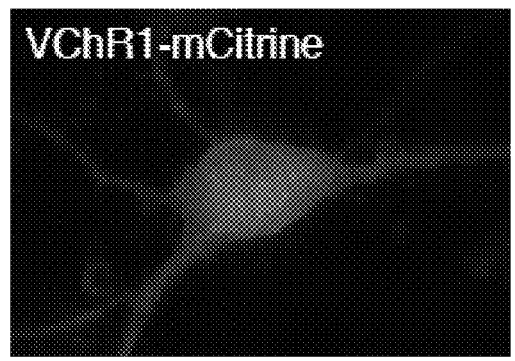
Figure 7D:
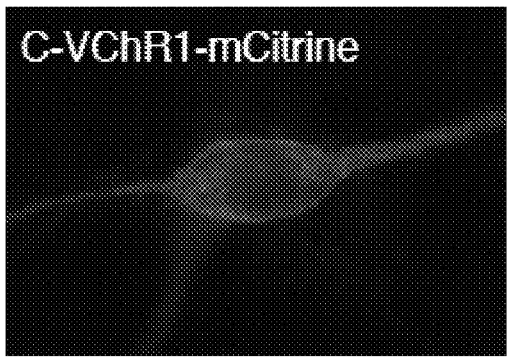
Figure 7E:
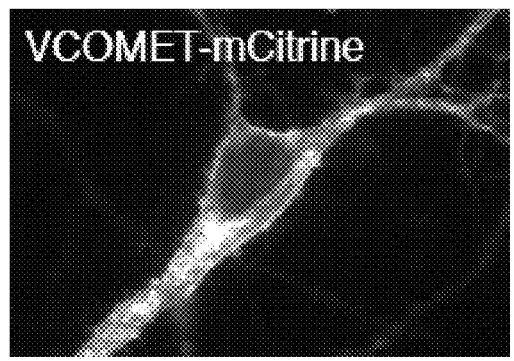

The ChETA mutation (Gunaydin, L. A. et al., Nat Neurosci 13, 387-392 (2010)) did not red-shift nor reduced the desensitization of VCOMET. The corresponding H134R mutation of ChR2 17 slowed the channel kinetics, a feature unfavorable for most experiments. One of the mutations, L171I, corresponding to the same position of the ChIEF mutation (Lin, J. Y. et al., Biophys J 96, 1803-1814 (2009)), increased the amplitudes of photo-response to 610 and 630 nm light (FIGS. 6F and 10). This mutation led to a red-shift in the action spectra and a steady-state/plateau spectral peak at 630 nm. Due to the strong response of this variant to orange and red light above 600 nm, we named this variant Red-activatable Channelrhodopsin (ReaCh). ReaCh retained the reversal potential (7.4±3.6 mV, n=6), reduced inward rectification (not shown), photocurrent amplitudes (33.5±3.6 pA/pF; n=9) and membrane trafficking and expression of VCOMET (FIG. 1b-d). One limitation of ReaCh, is the slower channel closure rate after the termination of the light pulse relative to VCOMET and C-VChR1 (time constants of 137.2±7.0 ms, n=11, compared to 84.9±3.7 ms for C-VChR1, n=9 and 100.4±6.6 ms for VCOMET, n=9; FIG. 2d).

Channelrhodopsin chimeras and point mutants were generated with over-lapping polymerase-chain reaction with the phusion PCR mix (New England Biolabs, Ipswich, Mass., USA). Standard digestion and ligation techniques were used to insert the mutant into the expression vector.

For experiments with HEK293 cells, the channelrhodopsin variants were expressed with pcDNA3.1 vector under the CMV promoter and cells were transfected with Fugene HD (Roche, Basel, Switzerland). In the experiments measuring membrane expression of channelrhodopsins in primary cultured neurons, channelrhodopsins-mCitrine were expressed under the CAG promoter with a WPRE sequence inserted after the stop codon of the mCitrine coding sequence, and electroporated into the neurons prior to plating (Lonza, Walkersville, Md.). For the stimulation of cultured primary hippocampal neurons with red-light, ReaCh-mCitrine was introduced with a lentivirus.

Example 3

Lentivirus and Recombinant Adeno-Associated Virus (rAAV) Production

ReaCh-mCitrine was subcloned into a generation 2 lentiviral construct with an hSynapsin promoter. The ReaCh-mCitrine lentivirus was made according to the protocols published on the Salk Institute's Gene Transfer Targeting and Therapeutics Core website, with minor modification. Briefly, 293A cells (Life Technologies, Carlsbad, Calif.) were grown to 85% confluence and transfer vector containing ReACh-mCitrine, psPAX2, and pMD2.G (gifts from Dr. Didier Trono, Ecole Polytechnique Fédérale de Lausanne) were transfected with calcium phosphate approach (Clontech, Mountain View, Calif.). Virus particles were harvested from serum-free medium and concentrated with 20% sucrose cushion with ultracentrifugation. The titer of lentivirus was estimated with Lentivirus Rapid Quantitation Kit (Cell Biolabs Inc. San Diego Calif., USA) to be $1.7 \times 10^9$ virus particles/mL. The Lentiviral vector was a gift from Dr. Ed Boyden, MIT).

rAAV8 containing ReACh-mCitrine was produced and purified, according to protocols published on the Salk Institute's Gene Transfer Targeting and Therapeutics Core website, by transfected AAV2 ITR vector (gift from Dr. Lin Tian, Howard Hughes Medical Institute Janelia Farm Research Campus) containing ReACh-mCitrine, and the helper plasmids XX6-80 and XR8 (National Vector Biorepository) into 293A cells. rAAV2/8 were released from the cells by freeze-thawing and purified with iodixanol gradient purification. The virus was further concentrated using Amicon Ultra centrifugal filter (Millipore, Billerica, Mass.) with 50 kDa cut-off. The rAAV titer was measured by the Salk Vectorcore service with qPCR technique and is estimated to be $3 \times 10^{13}$ GC/mL.

Example 4

Measurement of Channelrhodopsin Membrane Expression

Channelrhodopsin membrane expression in HEK293 and cultured cortical neurons were measured by imaging on a Zeiss Live 5 Confocal microscope (Thornwood, N.Y.). Transfections and measurements of expression were performed with the same concentrations of DNA. The transfected cells were imaged with the same setting for comparison. The measurements of expression were performed on cells with detectable visible fluorescence and normal cell morphology non-discriminatively in the culture dish to ensure fair comparisons. Membrane expressions were measured by taking the mean fluorescence intensities of the membrane and the cytosol of the in-focus imaging plane with ImageJ software. In experiments where channelrhodopsin membrane currents were normalized to membrane fluorescence, images were acquired with an EMCCD camera (Photometric, Tucson, Ariz.) at 512×512 resolution in epifluorescence mode prior to electrophysiological recording.

Example 5

Cell Culture, Electrophysiological Recordings and Stimulation of Cultured Cells Characterization of spectral response, reversal potential, kinetics, and membrane trafficking of VCOMET, ReACh, CatCh and oChEF described herein were performed by whole-cell patch clamping on 293A cells 2 days after transfection. All recordings were performed with extracellular solution containing 118 mM NaCl, 3 mM KCl, 2 mM $CaCl_2$, 1 mM $MgCl_2$, 10 mM HEPES, 20 mM glucose (pH 7.35, 310 mOsm) and intracellular solution containing 110 mM CsMethanesulfonate, 30 mM Tetraethylammonium chloride, 10 mM EGTA, 10 mM HEPES, 1 mM $CaCl_2$, 1 mM $MgCl_2$, 2 mM Mg-ATP, 0.15 mM $Na_3$-GTP (pH 7.25, 285 mOsm), except for the reversal potential measurement where the intracellular solution contains 125 mM K-gluconate, 10 mM $K_4$-BAPTA, 5 mM NaCl, 1 mM $CaCl_2$, 10 mM HEPES, 2 mM MgATP and 0.3 mM Tris-GTP (pH 7.25, 285 mOsm). All chemicals were acquired from Sigma-Aldrich (St. Louis, Mo.).

Light induced action depolarization studies were performed on 17-20 DIV neurons extracted from P2 neonatal Sprague-Dawley rat pups after 9 days of infection with lentivirus. Recording in cultured neurons were performed in current clamp mode with current injected to sustain −65 mV membrane potential at rest. The neuronal recording were done with K-gluconate based pipette solution and NaCl-based extracellular solution described above with the addition of 10 µM NBQX, 10 µM bicuculline and 20 µM APV in the extracellular solution to block fast synaptic transmission (Tocris, Ellisville, Mo.). Recordings were performed with Axopatch 200B patch clamp amplifier (Molecular Devices, Union City, Calif.) and acquired through Digidata 1320 (Molecular Devices) to a PC (Dell, Austin, Tex.) running pClamp 9.2 software (Molecular Devices). Analysis was conducted with AxographX (Sydney, New South Wales, Australia) and Graphpad Prism 4.0 (San Diego, Calif.).

With the characterization in HEK293 cells, only cells with high membrane resistance and low series resistance were used. Series resistance were compensated 70-80% when measuring the kinetics and reversal potentials. Junction potentials were not corrected.

Light stimulation was provided from a monochromator xenon light source (Polychrome IV, TILL Photonic, Victor, N.Y.) with 15 nm half-width. Shuttering and intensity of light were controlled with a custom-fitted 25 mm mechanical shutter (Vincent Associates, Rochester, N.Y.) and a neutral density wheel (Thorlab, Newton, N.J.). For the spectral response measurements and experiments where light intensity was not described, cells were stimulated with light $\sim 5.1 \times 10^{16}$ photon/$mm^2$/s across the light spectra. The response spectra of ChRs were measured with a 1 s light pulse from 650 nm to 410 nm of the same photon flux at 20 nm intervals, with maximum response as the maximal photocurrent obtained within the 1 s pulse at the described wavelength and the steady-state response measured between 0.95-1 s after the onset of the stimulation light pulse.

Comparisons of the properties of channelrhodopsin variants were done with one-way ANOVA followed by 2-tailed Tukey's tests between all pairs compared on Graphpad Prism 4.0 (San Diego, Calif.). All graphs are presented as Mean±SEM.

Example 6

Expression and Stimulation of Channelrhodopsin-Expressing Neurons In Vivo

Lentivirus or rAAV2/8 were injected stereotaxically into the vibrissal motor (vM1) cortex and the facial motor nucleus (FN) of C57BL/6 mice using a nano-liter injector (Nanoject II, Drummond, Broomall, Pa.) under isofluorane anaesthesia. Injection coordinates for vM1 cortex was 1 mm posterior, 1 mm lateral, and 0.8 mm ventral, and for FN 5.8 mm posterior, 1 mm medial, and 6 mm ventral to bregma. Lentivirus and rAAV2/8 was injected in 10×50 nl aliquots every 5 minutes (total volume 500 µl) in vM1, and in 5×12 µl aliquots (total volume 60 µl) every 5 minutes in the FN. After a waiting period of 2-5 weeks, ReACh expression was confirmed with epifluoresence imaging of vM1, and histologically against a fluorescent Nissl counterstain in both vM1 and FN (NeuroTrace Cat# N21479, Life Technologies, Carlsbad, Calif.). One day prior to experiments, a head-bar was attached to the skull using cyanoacrylate gel covered with layer of dental acrylic. The following days, mice were head-fixed either when awake or during isoflurane (0.5-2%), as indicated. ReaCh was activated in vivo by light-emitting diodes (LEDs) (470 nm, 617 nm, 627 nm and 655 nm; Luxeonstar, Brantford, Ontario, Canada) connected to a computer-controlled current source (Mightex; Pleasanton, Calif.), or by a 635 nm diode laser (30 mW, Coherent, Santa Clara, Calif.). Laser light was shuttered mechanically (Vincent Associates, Rochester, N.Y.), coupled into a multi-mode optical fiber and focused on the cortical surface to a 200 μm spot. The power of incident laser illumination was 60 mW/mm$^2$ Electrophysiological recordings and movies of vibrissa movement were acquired on a PC computer running Matlab (Mathwork, Natick, Mass.) as previously described (Drew, P. J. et al., *Chronic Nat Methods* 7, 981-984 (2010)). Vibrissa movements were monitored with high speed video and tracked offline using the Whisker-Tracker software (Knutsen, P. M. et al., *J Neurophysiol* 93, 2294-2301 (2005)). All animal procedures were approved by the UCSD Institutional Animal Care and Use Committee.

Example 7

Comparison of Red-Shifted Channelrhodopsin with C1V1 and C1V1(E122T) Variants A recently published channelrhodopsin variant, C1V1 (E122T), has been shown to excite neuronal membrane potential with 630 nm light pulsed for 50 ms (Yizhar, O. et al., *Nature* 477, 171-178 (2011)). This variant, and the parent C1V1 polypeptide, were directly compared to VCOMET and ReaCh variants provided herein. The results indicate that C1V1 photocurrent by approximately 3 fold (4.4±0.6 pA/pF, n=10; FIG. 6E), although its response spectra are red-shifted, with spectral peaks at 600 nm and 610 nm for the maximum and steady-state/plateau responses, respectively (FIGS. 6C, D, and F).

Moreover, the channel kinetics of C1V1(E122T) are significantly slower than VCOMET, ReaCh or C-VChR1, with channel closure time constants of 315.4±26.0 ms (n=8), although not significantly different from C1V1 (306.3±10.3 ms, n=6; FIG. 10I). The channel on-rate time constant of C1V1(E122T) is also 1.5- to 3-folds slower than ReaCh and CVChR1 at the same light intensities in response to 610 and 630 nm light (FIGS. 10G and H).

The light sensitivities of C-VChR1, ReaCh and C1V1 (E122T) are similar with regards to channel activation (FIG. 11). Interestingly, increasing the stimulation intensity of 610 nm light leads to the reduction of steady-state/plateau response amplitudes of all three channelrhodopsins at higher light intensities (FIGS. 10A-C and 11A-I).

These results demonstrate that ReaCh has improved membrane trafficking, greater photocurrent, and faster kinetics compared to C1V1(E122T). Accordingly, ReaCh is better suitable for the stimulation of neurons with red/red-orange light.

Electrophysiological characterizations shown in Table 2 were made under voltage-clamp recordings in HEK293 cells, where the membrane potential can be accurately clamped at −60 mV. Membrane fluorescence and cytosol fluorescence were measured in HEK293 cells transiently expressing the channelrhodopsin fused to mCitrine imaged with a confocal laser-scanning microscope.

TABLE 2

Comparisons of the channel kinetics and properties of C-VChR1, VCOMET, ReaCh, C1V1, and C1V1(E122T).

| Variant | Response spectra (nm) Maximum | Response spectra (nm) Steady-state | Mean membrane fluorescence (A.U.) | Mean membrane/cytosol fluorescence ratio | Mean photocurrent (pA/pF) | Channel on-rate τ (ms) 610 nm at 7.6 mW/mm$^2$ | Channel on-rate τ (ms) 630 nm at 7.6 mW/mm$^2$ | Channel off-rate τ (ms) |
|---|---|---|---|---|---|---|---|---|
| C-VChR1 | ~570 | ~530 | 18 ± 11 (n = 29) | 0.98 ± 0.07 (n = 29) | 5.9 ± 1.1 (n = 13) | 19.4 ± 0.8 (n = 11) | 49.4 ± 2.0 (n = 10) | 84.9 ± 3.9 (n = 11) |
| VCOMET | ~590 | ~530 | N/D | 1.10 ± 0.07 (n = 26)++ | 38.9 ± 7.8 (n = 13) | N/D | N/D | 100.4 ± 6.6 (n = 9) |
| ReaCh | ~590 | ~630 | 118 ± 29 (n = 21) | 1.12 ± 0.07 (n = 21) | 31.3 ± 3.6 (n = 9) | 20.7 ± 0.6 (n = 11) | 68.1 ± 4.2 (n = 10) | 137.2 ± 7.1 (n = 11) |
| C1V1 | N/D | N/D | 87 ± 17 (n = 26) | 0.70 ± 0.06 (n = 26) | 13.0 ± 3.0 (n = 10) | N/D | N/D | 306.3 ± 10.3 (n = 6) |
| C1V1 (E122T) | ~600 | ~610 | 72 ± 11 (n = 16) | 0.58 ± 0.06 (n = 16) | 4.4 ± 0.6 (n = 10) | 41.5 ± 4.6 (n = 7) | 115.8 ± 11.1 (n = 6) | 115.4 ± 26.0 (n = 8) |

N/D: not determined.
++ indicates the value of VCOMET was acquired in a separate experiment with different pixel dwelling time settings.

VCOMET and ReaCh possesses advantageous qualities not shared with C1V1 or C1V1(E122T) (Table 2).

C1V1 and C1V1(E122T) both expressed strongly in HEK293 cells, as visualized with mCitrine fluorescence of the C-terminal fusion protein. However, C1V1 and C1V1 (E122T) did not traffic to the membrane as well as ReaCh or VCOMET, with high levels of intracellular aggregation and strong cytosolic fluorescence commonly observed (FIG. 6B).

Further, the mean photocurrent of C1V1 is significantly smaller (13.0±3.0 pA/pF, n=10) than VCOMET or ReaCh in HEK293 cells (FIG. 6E), possibly caused by reduced efficiency in trafficking to the cell outer membrane (FIGS. 6C and D). Introduction of the E122T mutation reduced the

Example 8

Utilization of ReaCh to Excite Neurons with Red and Red-Orange Light In Vivo To test the utility of ReaCh to induce supra-threshold depolarization in neurons, a ReaCh construct fused at its C-terminus to mCitrine was expressed in cultured hippocampal neurons with a lentiviral vector under the neuron specific human synapsin promoter (hSyn). Neurons with detectable expression of mCitrine were tested non-discriminatively. Results from neurons with various expression levels and cell types (as assessed with membrane properties, spiking profile and morphology) were included.

Briefly, current was injected through the patch-pipette to sustain the membrane potentials of all cells at −65 mV (junction potential not corrected). Supra-threshold depolarization was achieved with red-orange light at 610 nm and 617 nm and red light at 630 nm in most ReaCh-expressing culture neurons in response to 750 ms light pulses (FIGS. 12A and B; FIG. 13). The level of depolarization and spike-delayed time was dependent on the wavelength, light intensity and expression level, in addition to the membrane properties of the neurons (cell type, membrane resistance and capacitance), as expected.

Using 610 nm and 617 nm light, depolarization to ~−20 mV was achieved (FIGS. 12E and F; FIG. 13). Trigger action potentials with <10 ms delay were achieved when ReaCh was expressed at high levels and stimulated with high light intensity (FIGS. 12G and H; FIG. 13).

Likewise, using 630 nm light, approximately −25 mV depolarization and spike delays <20 ms light where achieved in high expressing cells, although the depolarization was insufficient to evoke spikes in low expressing cells.

ReaCh-expressing cultured hippocampal neurons were then stimulated with 610 nm, 617 nm, or 630 nm light at 10 Hz (5 ms or 10 ms pulse width controlled by a mechanical shutter). Pulsed stimulation was also effective in triggering spikes in expressing neurons, but due to the slower kinetics and strong response of ReaCh to 610 nm and 617 nm light, the triggering of action potentials by pulsed light was not as temporally precise as with blue-light activated channel-rhodopsin variants such as ChIEF, which has minimal desensitization and faster channel kinetics (onset time constant <3 ms and off-rate time constant ~12 ms; Lin, J. Y. et al., *Biophys J* 96, 1803-1814 (2009)) (FIG. 12).

At high light intensities, extra action potentials and insufficient repolarization between light pulses were the main reasons for loss in temporal fidelity. In response to 617 nm and 630 nm light pulses, the loss of temporal fidelity was often due to insufficient depolarization in response to short light pulses e.g., 10 ms, relative to the slow onset kinetics and lower light sensitivity, especially in response to early light pulse stimulation. However, 100% fidelity was still observed in some ReaCh-expressing cells stimulated with 10 Hz light pulses at 610 nm, 617 nm or 630 nm.

Figures 15A, 15B, 15C:
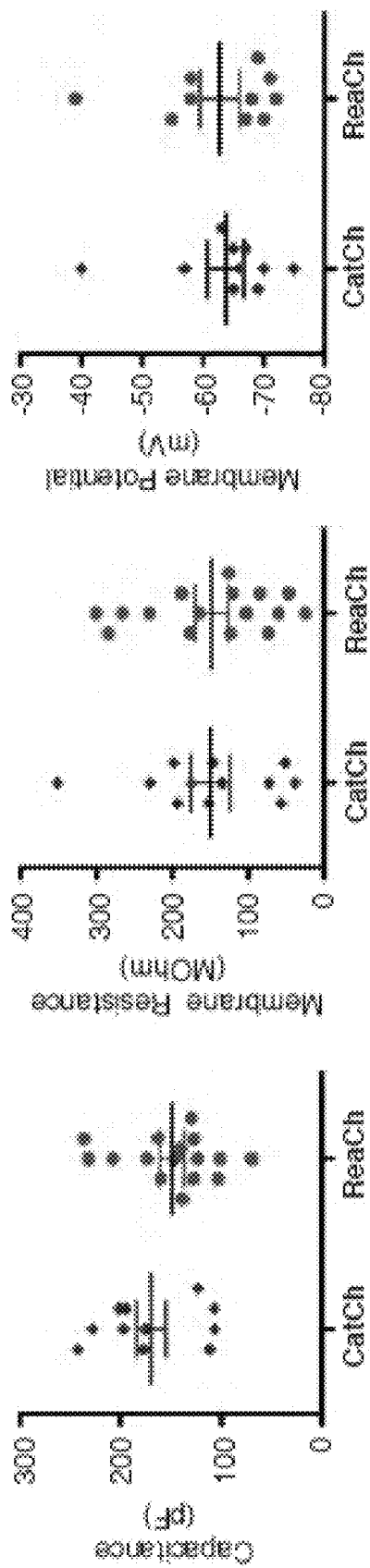
FIG. 15 shows the membrane properties of ReaCh-expressing primary culture hippocampal neurons, as compared to ChR2/CatCh-expressing neurons. The mean capacitance (A), membrane resistance (B), and membrane potentials (C) were not significantly different for the two groups.

Trigger action potentials were also achieved in ReaCh-expressing neurons using 470 nm light (FIG. 14) at low light intensities. The membrane properties (capacitance, membrane potential, and membrane resistance) of the ReaCh-expressing neurons were not significantly different from ChR2/CatCh-expressing neurons (FIG. 15).

Although cultured cells were not shielded from ambient light prior and during experiments, the cells retained normal morphological appearances and physiological membrane properties. This suggests that there are little or no toxic effect associated with the expression of ReaCh using the hSyn promoter.

Example 9

Excitation of Neurons with Red and Red-Orange Light In Vivo

As red light can penetrate mammalian tissues in vivo with less attenuation compared to blue or green light (Tromberg, B. J. et al., *Neoplasia* 2, 26-40 (2000)), the red-shifted channelrhodopsin polypeptide ReaCh was used to stimulate deep brain structures in vivo. Two areas were targeted for in vivo stimulation: 1) layer Vb of the vibrissa motor cortex (vM1), which contains motoneurons involved in the control and execution of vibrissae motion (Hill, D. N. et al., *Neuron* 72, 344-356 (2011); and Boyden, E. S. et al., *Nat Neurosci* 8, 1263-1268 (2005)) the facial motor nucleus of the 7$^{th}$ cranial nerve, whose motoneurons innervate muscles responsible for movements of the vibrissae.

Figure 16A:
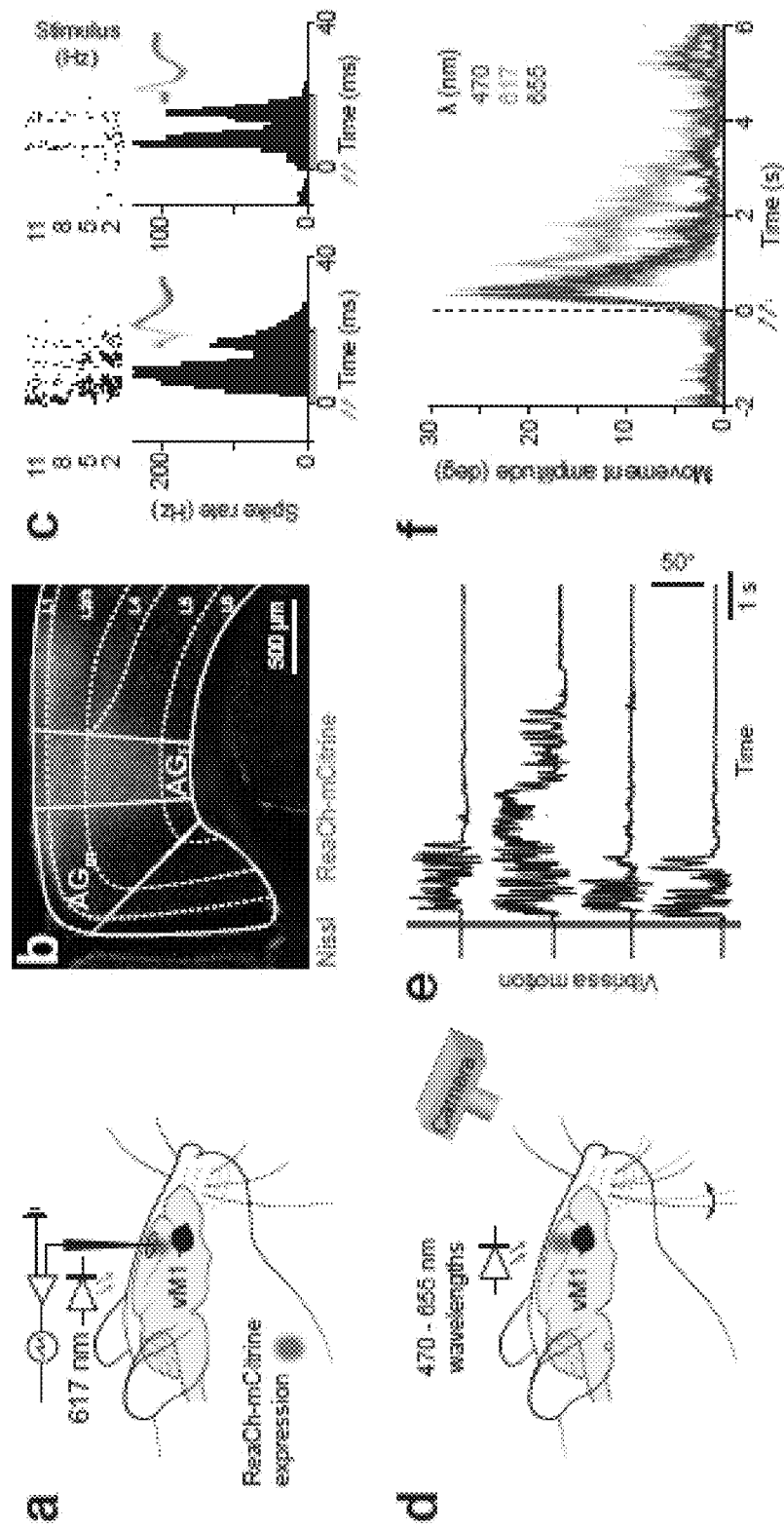
FIG. 16A-B show in vivo expression and utilization of ReaCh for triggering of action potentials and vibrissa movements. (a) Schematic of vM1 cortex stimulation and recording experiment. ReaCh-mCitrine (green) was expressed in vM1 cortex and single-units recorded with a high impedance (10 MΩ) tungsten electrode. Vibrissa movements were recorded with a high-speed video camera. (b) Histological identification of rAAV mediated ReaCh expression in layer Vb neurons of vM1 cortex visualized with mCitrine fluorescence (green) and Niss1 staining (blue). (c) Representative single-unit recordings in anesthetized (left) and awake (right) mice expressing ReaCh-mCitrine in layer Vb vM1 cortical neurons. Action potentials (black dots) were evoked by 20 ms pulses at 2 to 11 Hz of 617 nm light from an LED placed above the exposed cortex. Peristimulus time histograms (PSTH) demonstrate robust and temporally precise activation of infected neurons. (d) Schematic of vM1 cortical stimulation in the awake, head-fixed mouse. LEDs were placed on top of the ReaCh expression site above closed cranial window and healed skin. (e) Four individual trials of vibrissa movements by an awake, head-fixed mouse evoked by a single 100 ms pulse of 617 nm LED light (red bar). Increase in angle denotes protraction of the vibrissae. (f) Averaged evoked movement amplitudes after stimulation with 617 nm, 655 nm and 470 nm light (100 ms pulse). (g) Schematic of brainstem stimulation in the head-fixed, awake and anesthetized mouse. ReaCh was activated by placing an LED at the entrance of the ear-canal ipsilaterally to the site of rAAV injection in the brainstem. The LED was oriented parallel to the interaural line. (h) Coronal section through FN of a mouse expressing ReaCh-mCitrine (green) in motoneurons. (i) Vibrissa movements (measured in degrees) evoked by stimulating ReaCh expressing motoneurons in the lateral FN with 470 nm and 617 nm light. (j) Vibrissa retractions evoked of stimulation of FN motoneurons with 470 nm and 617 nm light. (k) The vibrissae movements of the animal shown in (j), elicited by 617 nm and 470 nm light at different illumination intensities. (l) Vibrissa protractions evoked of stimulation of FN motoneurons with 617 nm and 470 nm light. (m) The vibrissae movements of the animal shown in (l), elicited by 617 nm, 627 nm, 655 nm and 470 nm light at increasing illumination intensities. 655 nm and 470 nm light did not evoke detectable movements.

Briefly, ReaCh-mCitrine was incorporated into either a lentiviral or a recombinant adeno-associated virus (rAAV) with a hSynapsin promoter, and injected into a single region of individual mice. ReaCh expression in vM1 injected mice was confirmed 2-5 weeks post-injection, and the zone of infection mapped by epifluorescence imaging of the cortical surface. The mice were headfixed and vibrissa motion monitored with high-speed video either during light isoflurane (1-1.5% (v/v)) anaesthesia or while the mice were awake (FIG. 16A, panel a). The cortical surface above the zone of ReaCh expression (FIG. 16A, panel b) was illuminated with 20 ms pulses of 617 nm red-orange light from an light emitting diode (LED) during electrophysiological recordings (FIG. 16A, panel a and c). Lentivirus infected layer 5 vM1 neurons (800-1000 µm below the surface) were reliably activated, in both awake and anesthetized mice, with typical spike delays of <5 ms at stimulation frequencies from 2 to 11 Hz (FIG. 16A, panel c). Activation with 20 ms pulses usually resulted in multiple spikes for the duration of the stimulus, suggesting the neurons spiked both during the peak and steadystate/plateau phases of ReaCh induced photocurrents. Despite good expression, vibrissa movements could not be evoked in lentivirus infected mice, presumably as a result of limited spread of the infected area from our single- or dual-site injections.

In contrast, a larger and denser ReaCh expression was observed in vM1 cortex when mice were infected with rAAV and, in this case, vibrissa motion could be elicited upon stimulation with 617 nm or 655 nm LED light placed above the healed skull and skin (FIG. 16A, panels d-f). The evoked whisker motion was characteristic of that found with electrical stimulation of vM1, with both a rapid component (Berg, R. W. & Kleinfeld, D., *J Neurophysiol* 90, 2950-2963 (2003); and Brecht, M. et al., *Nature* 427, 704-710 (2004)) and a sustained period of whisking activity that outlasted the stimulus (Haiss, F. & Schwarz, C., *J Neurosci* 25, 1579-1587 (2005)) (FIG. 16A, panel f). Thus, ReaCh can serve as an efficient replacement of electrical stimulation for stimulating deep cortical layers.

Figure 16B:
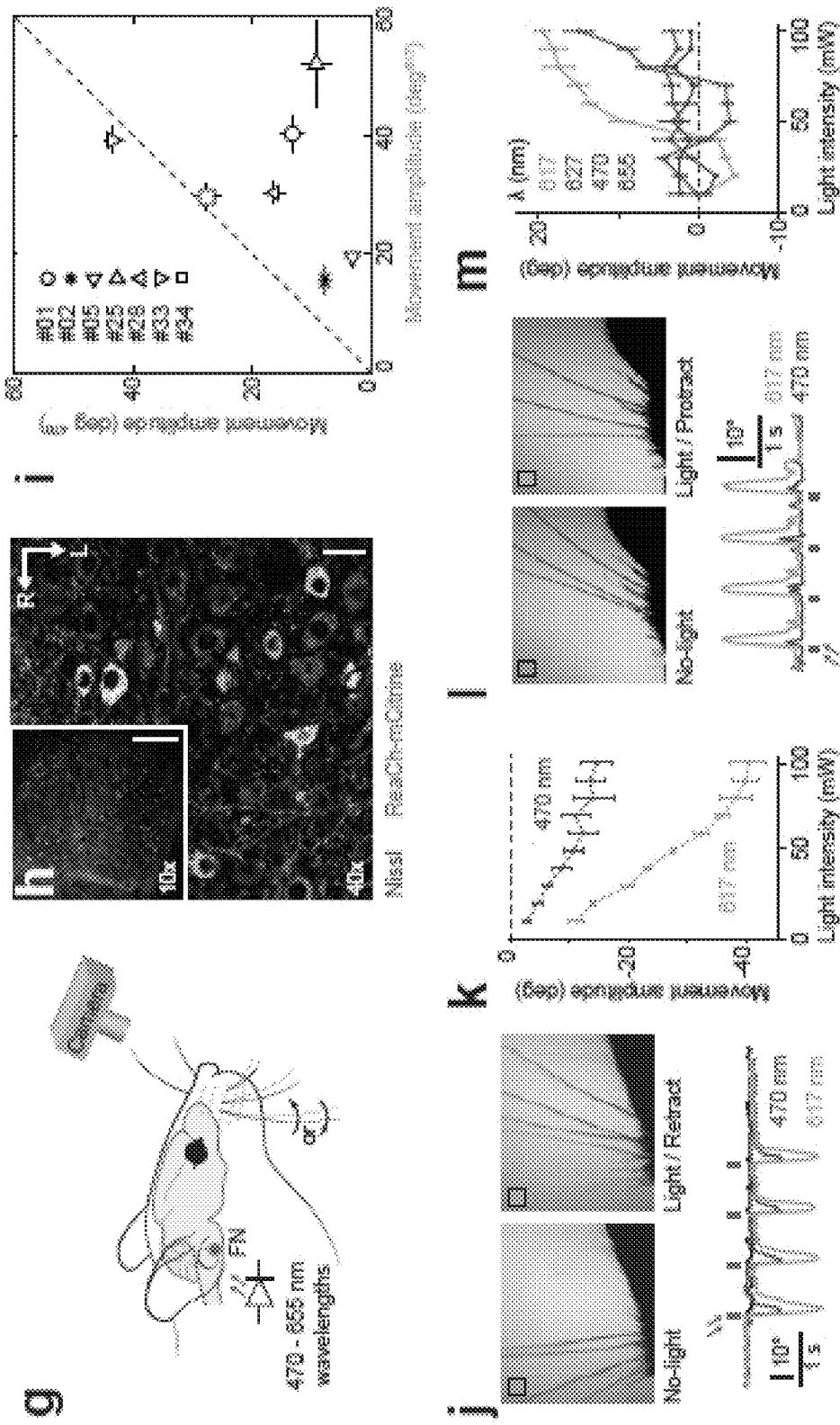

Next, ReaCh was expressed in the facial motor nucleus (FN) of the 7th cranial nerve by stereotaxic injection of rAAV with a hSynapsin promoter. In mice, the facial nucleus is located at a depth of up to 6 mm in the ventral part of brainstem, in proximity to other brainstem nuclei involved in regulation of vital functions, which complicates light delivery with invasive optical fibers. To circumvent these difficulties, we delivered light (470 nm, 617 nm, 627 nm and 655 nm) in a noninvasive manner by placing an LED at the entrance of the ear-canal, and thus directly illuminating through intact tissue and bone (FIG. 16B, panel g). Depending on the location and volume of the AAV injection, ReaCh could be expressed either uniformly or partially throughout the facial nucleus.

Activation of ReaCh expressing neurons elicited highly reproducible and temporally precise vibrissa movements, consistent with direct activation of motoneurons (FIG. 16B, panels i-l). The behavioral outcome of ReaCh activation differed as a function of injection site. For example, when ReaCh was expressed throughout the FN (FIG. 16B, panel h), illumination at 617 nm through the aural cavity elicited large (>40°) retractions of all vibrissae (FIG. 16B, panel k and l).

Movements were also elicited with blue light at 470 nm, but were approximately 2.5-fold smaller in most cases.

In two animals, 470 nm light elicited as robust movements as 617 nm, presumably due to the higher expression levels of ReaCh in these animals. By comparison, when ReaCh was expressed primarily in the lateral subnucleus of the FN, where motoneurons innervating protractor muscles are located (Klein, B. G. & Rhoades, R. W., *J Comp Neurol* 232, 55-69 (1985)), the vibrissae retracted at low intensities and protracted at high intensities of 617 nm illumination (20 to 40 versus 50 to 100 mW; FIG. 16B, panel j). The larger protraction component suggests that motoneurons involved in both protraction and retraction were infected, while the reversal of response could reflect the segregation of motoneurons (Klein, B. G. & Rhoades, R. W., *J Comp Neurol* 232, 55-69 (1985)) that drive protraction versus retraction muscles (Hill, D. N. et al., *J Neurosci* 28, 3438-3455 (2008)).

Illumination with red light at 627 nm also evoked reliable vibrissa movement, although higher intensities were required as compared to illumination with 617 nm light. Illumination at the same intensity with blue light at 470 nm and far red light at 655 nm resulted in, on average, 4- and 4.5-fold smaller vibrissa movement, as compared to vibrissa movement induced by illumination with 617 nm light (FIG. 16B, panel m). The smaller vibrissae movements observed with 470 nm light are consistent with the greater attenuation of blue light by tissue.

Two mice having identical viral delivery of hChR2/H134R-EYFP into the FN were tested by illumination with 470 nm light. Despite similar expression pattern and level in these animals, 470 nm light failed to elicit any detectable movements in these animals.

Discussion of Experimental Results

As demonstrated above, new channelrhodopsin variants are provided that responds strongly to long wavelengths of visible light. This capability enables the depolarization of neurons in vivo through the intact skull in neocortex as well as in brainstem. Transcranial stimulation is essential for many chronic studies, in which cranial windows lead to activated microglia and astrocytes as part of an inflammatory response (Xu, H. T. et al., *Nat Neurosci* 10, 549-551 (2007), the content of which is hereby expressly incorporated by reference in its entirety for all purposes) that in turn alters neuronal physiology (Hauss-Wegrzyniak, B. et al., *Exp Neurol* 176, 336-341 (2002)) and plasticity (Grutzendler, J. et al., *Nature* 420, 812-816 (2002)) as well as pial vasculature (Sohler, T. P. et al., *Journal of Pharmacology and Experimental Therapeutics* 71, 325-330 (1941); Drew, P. J. et al., *Nature Methods* 7, 981-984 (2010); Sohler, T. P. et al., *Journal of Pharmacology and Experimental Therapy* 71, 325-330 (1941); and Drew, P. J. et al., *Chronic Nat Methods* 7, 981-984 (2010)). As outlined above, the channelrhodopsin variant ReaCh was introduced through injections of an engineered virus.

In one embodiment, specific populations of neurons are be labeled via retrograde transport of ReaCh from a known target (Osakada, F. et al., *Neuron* 71, 617-631 (2011); Gradinaru, V. et al., *Journal of Neuroscience* 27, 14231-14238 (2007); Gradinaru, V. et al., *Journal of Neuroscience* 27, 14231-14238 (2007); and Osakada, F. et al., *Neuron* 71, 617-631 (2011)). For example, in one embodiment, pools of motoneurons in the brainstem or the spinal are be labeled via injection into specific muscles. In another embodiment, opposing muscle groups could be labeled with short- versus long-wavelength channelrhodopsins, to permit differential optical control of opposing muscle groups. The weak absorption of short-wavelengths by ReaCh will not compromise this strategy if the anatomically deeper motor pools are labeled with ReaCh. Taken together, the addition of ReaCh to the channelrhodopsin family will facilitate neuroprosthetic control through transcranial and possibly transvertebral stimulation. ReaCh also provides a good template on which to better engineer channelrhodopsin variants that respond to red-light in the future.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A polypeptide comprising a channelrhodopsin-1 (ChR1) domain, a Volvox carteri channelrhodopsin-1 (VChR1) domain and a Volvox carteri channelrhodopsin-2 (VChR2) domain, wherein said polypeptide comprises an amino acid sequence that is at least 95% identical to SEQ ID NO: 1.

2. The polypeptide of claim 1, wherein the polypeptide has the structure:

$X^1$-$X^2$-$X^3$-$X^4$ wherein $X^1$ is a ChR1 domain,
$X^2$ is a first VChR1 domain,
$X^3$ is a VChR2 domain and
$X^4$ is a second VChR1 domain.

3. The polypeptide of claim 2, wherein one or more of the domains $X^1$, $X^2$, $X^3$, and $X^4$ comprises 1, 2, 3, 4, or 5 amino acid substitutions relative to a corresponding wild-type domain.

4. The polypeptide of claim 3, wherein the amino acid substitution is at one or more positions selected from 163, 171, 174 and 266.

5. The polypeptide of claim 3, comprising one or more amino acid substitutions selected from Glu163Thr, Leu171Ile, Leu171Val, His174Arg, and Phe266Tyr.

6. The polypeptide of claim 1 further comprising a fluorescent polypeptide.

7. The polypeptide according to claim 1, comprising an L171I amino acid substitution.

8. The polypeptide of claim 1, comprising the amino acid sequence of SEQ ID NO:1.

9. The polypeptide of claim 1, comprising the amino acid sequence of SEQ ID NO:4.

10. The polypeptide of claim 1, wherein the polypeptide provides a photocurrent of at least 10 pA/pF upon photostimulation with light having a wavelength of at least 600 nm in HEK293 cells.

11. The polypeptide of claim 1, wherein the ratio of membrane to cytosol localization of the polypeptide is at least 1.0, when expressed in an HEK293 cell.

12. The polypeptide of claim 1, further comprising a fluorescent protein fused to the C-tertninus.

* * * * *

```
SEQUENCE LISTING

<160> NUMBER OF SEQ ID NOS: 5

<210> SEQ ID NO 1
<211> LENGTH: 350
<212> TYPE: PRT
<213> ORGANISM: Artificial Sequence
<220> FEATURE:
<223> OTHER INFORMATION: channelrhodopsin variant polypeptide VCOMET

<400> SEQUENCE: 1

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
        50                  55                  60

Val Ile Cys Ile Pro Asn Asn Gly Gln Cys Phe Cys Leu Ala Trp Leu
65                  70                  75                  80
```

Lys Ser Asn Gly Thr Asn Ala Glu Lys Leu Ala Ala Asn Ile Leu Gln
                85                  90                  95

Trp Val Val Phe Ala Leu Ser Val Ala Cys Leu Gly Trp Tyr Ala Tyr
            100                 105                 110

Gln Ala Trp Arg Ala Thr Cys Gly Trp Glu Val Tyr Val Ala Leu
            115                 120                 125

Ile Glu Met Met Lys Ser Ile Ile Glu Ala Phe His Glu Phe Asp Ser
    130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Pro Tyr Gly Ser Ala Ile Gly
            275                 280                 285

His Ser Ile Leu Asp Leu Ile Ala Lys Asn Met Trp Gly Val Leu Gly
        290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

```
<210> SEQ ID NO 2
<211> LENGTH: 1053
<212> TYPE: DNA
<213> ORGANISM: Artificial Sequence
<220> FEATURE:
<223> OTHER INFORMATION: polynucleotide encoding channelrhodopsin
      variant polypeptide VCOMET

<400> SEQUENCE: 2
accatggtga gcagaagacc ctggctgctg gccctggccc tggccgtggc cctggccgcc      60
ggcagcgccg cgccagcac cggcagcgac gccaccgtgc ccgtggccac ccaggacggc     120
cccgactacg tgttccacag agcccacgag agaatgctgt ccagaccag ctacaccctg     180 gagaacaacg gcagcgtgat ctgcatcccc aacaacggcc agtgcttctg cctggccctgg     240 ctgaagagta acggcaccaa cgccgagaag ctggccgcca acatcctgca gtgggtggtg     300
tttgcgctga gcgtggcgtg cctgggctgg tatgcgtatc aggcgtggcg cgcgacctgc     360
ggctgggaag aagtgtatgt ggcgctgatt gaaatgatga aaagcattat tgaagcgttt     420
catgaatttg atagcccggc gaccctgtgg ctgagcagcg gcaacggcgt ggtgtggatg     480
cgctatggcg aatggctgct gacctgcccc gtgctgctga ttcatctgag caacctgacc     540
```

```
ggcctgaaag atgattatag caaacgcacc atgggcctgc tggtgagcga cgtgggctgc      600
attgtgtggg gcgcgaccag cgcgatgtgc accggctgga ccaaaattct gttttttctg      660
attagcctga gctatggcat gtatacctat tttcatgcgg ccaaagtgta tattgaagcg      720
tttcataccg tgccgaaagg cctgtgcaga cagctggtga gagccatggc ctggctgttc      780
ttcgtgagct ggggcatgtt ccccgtgctg ttcctgctgg gccccgaggg cttcggccat      840
attagcccgt atggcagcgc gattggccat agcattctgg atctgattgc gaagaacatg      900
tggggcgtgc tgggcaacta tctgcgcgtg aaaattcatg aacatattct gctgtatggc      960
gatattcgca aaaacagaa aattaccatt gcgggccagg aaatggaagt ggaaaccctg     1020
gtggcggaag aagaagataa gtacgagagc agc                                 1053
```

<210> SEQ ID NO 3
<211> LENGTH: 9
<212> TYPE: DNA
<213> ORGANISM: Artificial Sequence
<220> FEATURE:
<223> OTHER INFORMATION: Kozak sequence

<400> SEQUENCE: 3 accatggtg                                                                9

<210> SEQ ID NO 4
<211> LENGTH: 350
<212> TYPE: PRT
<213> ORGANISM: Artificial Sequence
<220> FEATURE:
<223> OTHER INFORMATION: channelrhodopsin variant polypeptide ReaCh

<400> SEQUENCE: 4

```
Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
        50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Glu Met Met Lys Ser Ile Ile Glu Ala Phe His Glu Phe Asp Ser
    130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205
```

| | | | | | | | | | | | | | | |
|---|---|---|---|---|---|---|---|---|---|---|---|---|---|---|
| Cys | Thr | Gly | Trp | Thr | Lys | Ile | Leu | Phe | Phe | Leu | Ile | Ser | Leu | Ser | Tyr |
| | 210 | | | | 215 | | | | | 220 | | | | | |
| Gly | Met | Tyr | Thr | Tyr | Phe | His | Ala | Ala | Lys | Val | Tyr | Ile | Glu | Ala | Phe |
| 225 | | | | | 230 | | | | | 235 | | | | | 240 |
| His | Thr | Val | Pro | Lys | Gly | Leu | Cys | Arg | Gln | Leu | Val | Arg | Ala | Met | Ala |
| | | | | 245 | | | | | 250 | | | | | 255 | |
| Trp | Leu | Phe | Phe | Val | Ser | Trp | Gly | Met | Phe | Pro | Val | Leu | Phe | Leu | Leu |
| | | | 260 | | | | | 265 | | | | | 270 | | |
| Gly | Pro | Glu | Gly | Phe | Gly | His | Ile | Ser | Pro | Tyr | Gly | Ser | Ala | Ile | Gly |
| | | 275 | | | | | 280 | | | | | 285 | | | |
| His | Ser | Ile | Leu | Asp | Leu | Ile | Ala | Lys | Asn | Met | Trp | Gly | Val | Leu | Gly |
| | | 290 | | | | 295 | | | | | 300 | | | | |
| Asn | Tyr | Leu | Arg | Val | Lys | Ile | His | Glu | His | Ile | Leu | Leu | Tyr | Gly | Asp |
| 305 | | | | | 310 | | | | | 315 | | | | | 320 |
| Ile | Arg | Lys | Lys | Gln | Lys | Ile | Thr | Ile | Ala | Gly | Gln | Glu | Met | Glu | Val |
| | | | | 325 | | | | | 330 | | | | | 335 | |
| Glu | Thr | Leu | Val | Ala | Glu | Glu | Asp | Lys | Tyr | Glu | Ser | Ser |
| | | | 340 | | | | | 345 | | | | 350 |

```
<210> SEQ ID NO 5
<211> LENGTH: 1053
<212> TYPE: DNA
<213> ORGANISM: Artificial Sequence
<220> FEATURE:
<223> OTHER INFORMATION: polynucleotide encoding channelrhodopsin
      variant polypeptide ReaCh

<400> SEQUENCE: 5
accatggtga gcagaagacc ctggctgctg gccctggccc tggccgtggc cctggccgcc        60
ggcagcgccg cgccagcac cggcagcgac gccaccgtgc ccgtggccac ccaggacggc       120
cccgactacg tgttccacag agcccacgag agaatgctgt ccagaccag ctacaccctg        180
gagaacaacg gcagcgtgat ctgcatcccc aacaacggcc agtgcttctg cctggcctgg       240
ctgaagagta acggcaccaa cgccgagaag ctggccgcca acatcctgca gtgggtggtg       300
tttgcgctga gcgtggcgtg cctgggctgg tatgcgtatc aggcgtggcg cgcgacctgc       360
ggctgggaag aagtgtatgt ggcgctgatt gaaatgatga aaagcattat tgaagcgttt       420
catgaatttg atagcccggc gaccctgtgg ctgagcagcg gcaacggcgt ggtgtggatg       480
cgctatggcg aatggctgct gacctgcccc gtgattctga ttcatctgag caacctgacc       540
ggcctgaaag atgattatag caaacgcacc atgggcctgc tggtgagcga cgtgggctgc       600
attgtgtggg gcgcgaccag cgcgatgtgc accggctgga ccaaaattct gtttttttctg       660
attagcctga gctatggcat gtatacctat tttcatgcgg ccaaagtgta tattgaagcg       720
tttcataccg tgccgaaagg cctgtgcaga cagctggtga gagccatggc ctggctgttc       780
ttcgtgagct gggcatgtt ccccgtgctg ttcctgctgg gccccgaggg cttcggccat       840
attagcccgt atggcagcgc gattggccat agcattctgg atctgattgc gaagaacatg       900
tggggcgtgc tggcaacta tctgcgcgtg aaaattcatg aacatattct gctgtatggc       960
gatattcgca aaaaacagaa aattaccatt gcgggccagg aaatggaagt ggaaaccctg      1020
gtggcggaag aagaagataa gtacgagagc agc                                   1053
```